US008114613B2

(12) United States Patent
Caulfield

(10) Patent No.: US 8,114,613 B2
(45) Date of Patent: Feb. 14, 2012

(54) OXIDIZED APOA1 DETERMINATION BY MASS SPECTROMETRY

(75) Inventor: Michael P. Caulfield, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 13/039,261

(22) Filed: Mar. 2, 2011

(65) Prior Publication Data

US 2011/0223685 A1    Sep. 15, 2011

Related U.S. Application Data

(62) Division of application No. 11/489,265, filed on Jul. 18, 2006, now Pat. No. 7,972,794.

(51) Int. Cl.
*G01N 33/53* (2006.01)
(52) U.S. Cl. .......................... 435/7.1; 435/7.2
(58) Field of Classification Search ................. None
See application file for complete search history.

(56) References Cited

U.S. PATENT DOCUMENTS

| | | | |
|---|---|---|---|
| 5,756,291 | A | 5/1998 | Griffin et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koster |
| 6,309,888 | B1 | 10/2001 | Holvoet et al. |
| 2003/0113728 | A1 | 6/2003 | Salonen |
| 2005/0239136 | A1 | 10/2005 | Hazen et al. |
| 2006/0172429 | A1 | 8/2006 | Nilsson et al. |
| 2007/0099242 | A1 | 5/2007 | Heinecke et al. |

OTHER PUBLICATIONS

Barr et al., Isotope dilution-mass spectrometric quantification of specific proteins: model application with apolipoprotein A-I, Clinical Chemistry 42:10, pp. 1676-1682 (1996).
Bartolucci et al., Liquid chromatography tandem mass spectrometric quantitation of sulfamethazine and its metabolites: direct analysis of swine urine by triple quadrupole and by ion trap mass spectrometry. Rapid Communication in Mass Spectrometry, 14:967-973, 2000.
Bergt et al., Tyrosine Chlorination in Apo A-I is Directed by Lysine Residues When Hypochlorous Acid Oxidizes HDL, SFRBM 2003 Oxidation of Macromolecules DNA, Lipid, Protein, Carbohydrate, S101, Abstract No. 312.
Brennan et al., "Prognostic Value of Myeloperoxidase in Patients with Chest Pain", The New England Journal of Medicine, 349(17):1595-1604, 2003.
Chisolm et al., "The Oxidative Modification Hypothesis of Atherogenesis: An Overview", Free Radical Biology & Medicine, 28:1815-1826, 2000.
Garner et al., Oxidation of high density lipoproteins. Journal of Biological Chemistry, 273(11): p. 6080-6087, 1998.
Heinecke et al., "Oxidative Stress: New Approaches to Diagnosis and Prognosis in Atherosclerosis", American Journal of Cardiology, 91:12A-16A, 2003.
Heinecke et al., Detecting Oxidative Modification of Biomeolecules with Isotope Dilution Mass Spectrometry: Sensitive and Quantitative Assays for Oxidized Amino Acids in Proteins and Tissues, Methods in Enzymology, vol. 300, pp. 124-144.
International Search Report dated Sep. 11, 2008 in application PCT/US2007/073607.
Merchant et al., "Recent Advancements in Surface-Enhanced Laser Desorption/Ionization-time of Flight-Mass Spectrometry", Electrophoresis, 21:1164-67, 2000.
Navab et al., "Oxidized Lipids as Mediators of Coronary Heart Disease", Curr. Opin. Lipidol., 13:363-372, 2002.
Navab et al., The oxidation hypothesis of atherogenesis: the role of oxidized phospholipids and HDL, Journal of Lipid Research, vol. 45, 2004, pp. 993-1007.
Olsen et al.,"Trypsin Cleaves Exclusively C-Terminal to Arginine and Lysine Residues", Molecular & Cellular Proteomics, 3:608-614, 2004.
Pankhurst et al., Characterization of specifically oxidized apolipoproteins in mildly oxidized high density lipoprotein, Journal of Lipid Research, vol. 44, 2003, pp. 349-355.
Panzenboeck et al., Effects of Reagent and Enzymatically Generated Hypochlorite on Physicochemical and Metabolic Properties of High Density Lipoproteins, vol. 272, No. 47, Nov. 21, 1997, pp. 29711-29720.
Ross et al., "Atherosclerosis—An Inflammatory Disease", New England Journal of Medicine, 340:115-126, 2003.
US Notice of Allowance dated Dec. 1, 2010 in U.S. Appl. No. 11/489,265.
US Office Action dated Jul. 8, 2009 in U.S. Appl. No. 11/489,265.
Wright et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures", Prostate Cancer and Prostatic Diseases, 2:264-76, 1999.
Zheng et al., "Apolipoprotein A-I is a Selective Target for Myeloperoxidase-Catalyzed Oxidation and Functional Impairment in Subjects with Cardiovascular Disease", The Journal of Clinical Investigation, 114:259-541, 2004.
Zheng et al., "Localization of Nitration and Chlorination Sites on Apolipoprotein A-I Catalyzed by Myeloperoxidase in Human Atheroma and Associated Oxidative Impairment in ABCA1-dependent Cholesterol Efflux from Macrophages", The Journal of Biological Chemistry, 280:38-47, 2005.

*Primary Examiner* — Jacob Cheu
(74) *Attorney, Agent, or Firm* — Foley & Lardner LLP

(57) ABSTRACT

Methods are provided for the detection and quantitation of proteins generally and apolipoprotein A-I and oxidized derivatives thereof in particular. Further provided are methods for the assessment of the risk cardiovascular disease in a subject, wherein the assessment is based on the amount of oxidized and unoxidized apolipoprotein A-I in a biological sample obtained from a subject.

26 Claims, No Drawings

SEQUENCE LISTING

<160> NUMBER OF SEQ ID NOS: 98

<210> SEQ ID NO 1
<211> LENGTH: 267
<212> TYPE: PRT
<213> ORGANISM: Homo sapiens -continued

```
<400> SEQUENCE: 1

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95
```

Val Gln Pro Tyr Leu Asp Asp Phe Gln Lys Lys Trp Gln Glu Glu Met
              100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 11
<212> TYPE: PRT
<213> ORGANISM: Homo sapiens

<400> SEQUENCE: 3

Asp Glu Pro Pro Gln Ser Pro Trp Asp Arg Val
1               5                   10

<210> SEQ ID NO 4
<211> LENGTH: 13
<212> TYPE: PRT
<213> ORGANISM: Homo sapiens

<400> SEQUENCE: 4

Asp Glu Pro Pro Gln Ser Pro Trp Asp Arg Val Lys Asp
1               5                   10

<210> SEQ ID NO 5
<211> LENGTH: 24
<212> TYPE: PRT
<213> ORGANISM: Homo sapiens

<400> SEQUENCE: 5

Asp Glu Pro Pro Gln Ser Pro Trp Asp Arg Val Lys Asp Leu Ala Thr
1               5                   10                  15

Val Tyr Val Asp Val Leu Lys Asp
            20

<210> SEQ ID NO 6
<211> LENGTH: 15
<212> TYPE: PRT
<213> ORGANISM: Homo sapiens

<400> SEQUENCE: 6

Arg Val Lys Asp Leu Ala Thr Val Tyr Val Asp Val Leu Lys Asp
1               5                   10                  15

<210> SEQ ID NO 7
<211> LENGTH: 19
<212> TYPE: PRT

<213> ORGANISM: Homo sapiens

<400> SEQUENCE: 7

Arg Val Lys Asp Leu Ala Thr Val Tyr Val Asp Val Leu Lys Asp Ser
1               5                   10                  15

Gly Arg Asp

<210> SEQ ID NO 8
<211> LENGTH: 13
<212> TYPE: PRT
<213> ORGANISM: Homo sapiens

<400> SEQUENCE: 8

Lys Asp Leu Ala Thr Val Tyr Val Asp Val Leu Lys Asp
1               5                   10

<210> SEQ ID NO 9
<211> LENGTH: 17
<212> TYPE: PRT
<213> ORGANISM: Homo sapiens

<400> SEQUENCE: 9

Lys Asp Leu Ala Thr Val Tyr Val Asp Val Leu Lys Asp Ser Gly Arg
1               5                   10                  15

Asp

<210> SEQ ID NO 10
<211> LENGTH: 30
<212> TYPE: PRT
<213> ORGANISM: Homo sapiens

<400> SEQUENCE: 10

Lys Asp Leu Ala Thr Val Tyr Val Asp Val Leu Lys Asp Ser Gly Arg
1               5                   10                  15

Asp Tyr Val Ser Gln Phe Glu Gly Ser Ala Leu Gly Lys Gln
            20                  25                  30

<210> SEQ ID NO 11
<211> LENGTH: 19
<212> TYPE: PRT
<213> ORGANISM: Homo sapiens

<400> SEQUENCE: 11

Lys Asp Ser Gly Arg Asp Tyr Val Ser Gln Phe Glu Gly Ser Ala Leu
1               5                   10                  15

Gly Lys Gln

<210> SEQ ID NO 12
<211> LENGTH: 24
<212> TYPE: PRT
<213> ORGANISM: Homo sapiens

<400> SEQUENCE: 12

Lys Asp Ser Gly Arg Asp Tyr Val Ser Gln Phe Glu Gly Ser Ala Leu
1               5                   10                  15

Gly Lys Gln Leu Asn Leu Lys Leu
            20

<210> SEQ ID NO 13
<211> LENGTH: 15
<212> TYPE: PRT
<213> ORGANISM: Homo sapiens

```
<400> SEQUENCE: 13

Arg Asp Tyr Val Ser Gln Phe Glu Gly Ser Ala Leu Gly Lys Gln
1               5                  10                 15

<210> SEQ ID NO 14
<211> LENGTH: 20
<212> TYPE: PRT
<213> ORGANISM: Homo sapiens

<400> SEQUENCE: 14

Arg Asp Tyr Val Ser Gln Phe Glu Gly Ser Ala Leu Gly Lys Gln Leu
1               5                  10                 15

Asn Leu Lys Leu
            20

<210> SEQ ID NO 15
<211> LENGTH: 34
<212> TYPE: PRT
<213> ORGANISM: Homo sapiens

<400> SEQUENCE: 15

Arg Asp Tyr Val Ser Gln Phe Glu Gly Ser Ala Leu Gly Lys Gln Leu
1               5                  10                 15

Asn Leu Lys Leu Leu Asp Asn Trp Asp Ser Val Thr Ser Thr Phe Ser
            20                  25                 30

Lys Leu

<210> SEQ ID NO 16
<211> LENGTH: 21
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 16

Lys Xaa Leu Asn Leu Lys Leu Leu Asp Asn Trp Asp Ser Val Thr Ser
1               5                  10                 15

Thr Phe Ser Lys Leu
            20

<210> SEQ ID NO 17
<211> LENGTH: 21
<212> TYPE: PRT
<213> ORGANISM: Homo sapiens

<400> SEQUENCE: 17

Lys Gln Leu Asn Leu Lys Leu Leu Asp Asn Trp Asp Ser Val Thr Ser
1               5                  10                 15

Thr Phe Ser Lys Leu
            20

<210> SEQ ID NO 18
<211> LENGTH: 23
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 18

Lys Xaa Leu Asn Leu Lys Leu Leu Asp Asn Trp Asp Ser Val Thr Ser
```

```
                1               5                  10                 15
Thr Phe Ser Lys Leu Arg Glu
            20

<210> SEQ ID NO 19
<211> LENGTH: 23
<212> TYPE: PRT
<213> ORGANISM: Homo sapiens

<400> SEQUENCE: 19

Lys Gln Leu Asn Leu Lys Leu Leu Asp Asn Trp Asp Ser Val Thr Ser
1               5                  10                 15

Thr Phe Ser Lys Leu Arg Glu
            20

<210> SEQ ID NO 20
<211> LENGTH: 16
<212> TYPE: PRT
<213> ORGANISM: Homo sapiens

<400> SEQUENCE: 20

Lys Leu Leu Asp Asn Trp Asp Ser Val Thr Thr Phe Ser Lys Leu
1               5                  10                 15

<210> SEQ ID NO 21
<211> LENGTH: 18
<212> TYPE: PRT
<213> ORGANISM: Homo sapiens

<400> SEQUENCE: 21

Lys Leu Leu Asp Asn Trp Asp Ser Val Thr Thr Phe Ser Lys Leu
1               5                  10                 15

Arg Glu

<210> SEQ ID NO 22
<211> LENGTH: 34
<212> TYPE: PRT
<213> ORGANISM: Homo sapiens

<400> SEQUENCE: 22

Lys Leu Leu Asp Asn Trp Asp Ser Val Thr Thr Phe Ser Lys Leu
1               5                  10                 15

Arg Glu Gln Leu Gly Pro Val Thr Gln Glu Phe Trp Asp Asn Leu Glu
            20                  25                 30

Lys Glu

<210> SEQ ID NO 23
<211> LENGTH: 20
<212> TYPE: PRT
<213> ORGANISM: Homo sapiens

<400> SEQUENCE: 23

Lys Leu Arg Glu Gln Leu Gly Pro Val Thr Gln Glu Phe Trp Asp Asn
1               5                  10                 15

Leu Glu Lys Glu
            20

<210> SEQ ID NO 24
<211> LENGTH: 26
<212> TYPE: PRT
<213> ORGANISM: Homo sapiens

<400> SEQUENCE: 24
```

```
Lys Leu Arg Glu Gln Leu Gly Pro Val Thr Gln Glu Phe Trp Asp Asn
1               5                   10                  15

Leu Glu Lys Glu Thr Glu Gly Leu Arg Gln
                20                  25

<210> SEQ ID NO 25
<211> LENGTH: 18
<212> TYPE: PRT
<213> ORGANISM: Homo sapiens

<400> SEQUENCE: 25

Arg Glu Gln Leu Gly Pro Val Thr Gln Glu Phe Trp Asp Asn Leu Glu
1               5                   10                  15

Lys Glu

<210> SEQ ID NO 26
<211> LENGTH: 24
<212> TYPE: PRT
<213> ORGANISM: Homo sapiens

<400> SEQUENCE: 26

Arg Glu Gln Leu Gly Pro Val Thr Gln Glu Phe Trp Asp Asn Leu Glu
1               5                   10                  15

Lys Glu Thr Glu Gly Leu Arg Gln
                20

<210> SEQ ID NO 27
<211> LENGTH: 29
<212> TYPE: PRT
<213> ORGANISM: Homo sapiens

<400> SEQUENCE: 27

Arg Glu Gln Leu Gly Pro Val Thr Gln Glu Phe Trp Asp Asn Leu Glu
1               5                   10                  15

Lys Glu Thr Glu Gly Leu Arg Gln Glu Met Ser Lys Asp
                20                  25

<210> SEQ ID NO 28
<211> LENGTH: 13
<212> TYPE: PRT
<213> ORGANISM: Homo sapiens

<400> SEQUENCE: 28

Lys Glu Thr Glu Gly Leu Arg Gln Glu Met Ser Lys Asp
1               5                   10

<210> SEQ ID NO 29
<211> LENGTH: 19
<212> TYPE: PRT
<213> ORGANISM: Homo sapiens

<400> SEQUENCE: 29

Lys Glu Thr Glu Gly Leu Arg Gln Glu Met Ser Lys Asp Leu Glu Glu
1               5                   10                  15

Val Lys Ala

<210> SEQ ID NO 30
<211> LENGTH: 13
<212> TYPE: PRT
<213> ORGANISM: Homo sapiens
<220> FEATURE:
<221> NAME/KEY: MOD_RES
<222> LOCATION: (2)..(2)
```

<223> OTHER INFORMATION: Pyroglutamic acid

<400> SEQUENCE: 30

Arg Xaa Glu Met Ser Lys Asp Leu Glu Glu Val Lys Ala
1               5                   10

<210> SEQ ID NO 31
<211> LENGTH: 13
<212> TYPE: PRT
<213> ORGANISM: Homo sapiens

<400> SEQUENCE: 31

Arg Gln Glu Met Ser Lys Asp Leu Glu Glu Val Lys Ala
1               5                   10

<210> SEQ ID NO 32
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 32

Arg Xaa Glu Met Ser Lys Asp Leu Glu Glu Val Lys Ala Lys Val
1               5                   10                  15

<210> SEQ ID NO 33
<211> LENGTH: 15
<212> TYPE: PRT
<213> ORGANISM: Homo sapiens

<400> SEQUENCE: 33

Arg Gln Glu Met Ser Lys Asp Leu Glu Glu Val Lys Ala Lys Val
1               5                   10                  15

<210> SEQ ID NO 34
<211> LENGTH: 10
<212> TYPE: PRT
<213> ORGANISM: Homo sapiens

<400> SEQUENCE: 34

Lys Asp Leu Glu Glu Val Lys Ala Lys Val
1               5                   10

<210> SEQ ID NO 35
<211> LENGTH: 20
<212> TYPE: PRT
<213> ORGANISM: Homo sapiens

<400> SEQUENCE: 35

Lys Asp Leu Glu Glu Val Lys Ala Lys Val Gln Pro Tyr Leu Asp Asp
1               5                   10                  15

Phe Gln Lys Lys
            20

<210> SEQ ID NO 36
<211> LENGTH: 14
<212> TYPE: PRT
<213> ORGANISM: Homo sapiens

<400> SEQUENCE: 36

Lys Ala Lys Val Gln Pro Tyr Leu Asp Asp Phe Gln Lys Lys
1               5                   10

<210> SEQ ID NO 37
<211> LENGTH: 15
<212> TYPE: PRT
<213> ORGANISM: Homo sapiens

<400> SEQUENCE: 37

Lys Ala Lys Val Gln Pro Tyr Leu Asp Asp Phe Gln Lys Lys Trp
1               5                   10                  15

<210> SEQ ID NO 38
<211> LENGTH: 12
<212> TYPE: PRT
<213> ORGANISM: Homo sapiens

<400> SEQUENCE: 38

Lys Val Gln Pro Tyr Leu Asp Asp Phe Gln Lys Lys
1               5                   10

<210> SEQ ID NO 39
<211> LENGTH: 13
<212> TYPE: PRT
<213> ORGANISM: Homo sapiens

<400> SEQUENCE: 39

Lys Val Gln Pro Tyr Leu Asp Asp Phe Gln Lys Lys Trp
1               5                   10

<210> SEQ ID NO 40
<211> LENGTH: 22
<212> TYPE: PRT
<213> ORGANISM: Homo sapiens

<400> SEQUENCE: 40

Lys Val Gln Pro Tyr Leu Asp Asp Phe Gln Lys Lys Trp Gln Glu Glu
1               5                   10                  15

Met Glu Leu Tyr Arg Gln
            20

<210> SEQ ID NO 41
<211> LENGTH: 12
<212> TYPE: PRT
<213> ORGANISM: Homo sapiens

<400> SEQUENCE: 41

Lys Lys Trp Gln Glu Glu Met Glu Leu Tyr Arg Gln
1               5                   10

<210> SEQ ID NO 42
<211> LENGTH: 14
<212> TYPE: PRT
<213> ORGANISM: Homo sapiens

<400> SEQUENCE: 42

Lys Lys Trp Gln Glu Glu Met Glu Leu Tyr Arg Gln Lys Val
1               5                   10

<210> SEQ ID NO 43
<211> LENGTH: 11
<212> TYPE: PRT
<213> ORGANISM: Homo sapiens

<400> SEQUENCE: 43

Lys Trp Gln Glu Glu Met Glu Leu Tyr Arg Gln
1               5                   10

```
<210> SEQ ID NO 44
<211> LENGTH: 13
<212> TYPE: PRT
<213> ORGANISM: Homo sapiens

<400> SEQUENCE: 44

Lys Trp Gln Glu Glu Met Glu Leu Tyr Arg Gln Lys Val
1               5                   10

<210> SEQ ID NO 45
<211> LENGTH: 18
<212> TYPE: PRT
<213> ORGANISM: Homo sapiens

<400> SEQUENCE: 45

Lys Trp Gln Glu Glu Met Glu Leu Tyr Arg Gln Lys Val Glu Pro Leu
1               5                   10                  15

Arg Ala

<210> SEQ ID NO 46
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 46

Arg Xaa Lys Val Glu Pro Leu Arg Ala
1               5

<210> SEQ ID NO 47
<211> LENGTH: 9
<212> TYPE: PRT
<213> ORGANISM: Homo sapiens

<400> SEQUENCE: 47

Arg Gln Lys Val Glu Pro Leu Arg Ala
1               5

<210> SEQ ID NO 48
<211> LENGTH: 17
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 48

Arg Xaa Lys Val Glu Pro Leu Arg Ala Glu Leu Gln Glu Gly Ala Arg
1               5                   10                  15

Gln

<210> SEQ ID NO 49
<211> LENGTH: 17
<212> TYPE: PRT
<213> ORGANISM: Homo sapiens

<400> SEQUENCE: 49

Arg Gln Lys Val Glu Pro Leu Arg Ala Glu Leu Gln Glu Gly Ala Arg
1               5                   10                  15

Gln
```

```
<210> SEQ ID NO 50
<211> LENGTH: 15
<212> TYPE: PRT
<213> ORGANISM: Homo sapiens

<400> SEQUENCE: 50

Lys Val Glu Pro Leu Arg Ala Glu Leu Gln Glu Gly Ala Arg Gln
1               5                   10                  15

<210> SEQ ID NO 51
<211> LENGTH: 17
<212> TYPE: PRT
<213> ORGANISM: Homo sapiens

<400> SEQUENCE: 51

Lys Val Glu Pro Leu Arg Ala Glu Leu Gln Glu Gly Ala Arg Gln Lys
1               5                   10                  15

Leu

<210> SEQ ID NO 52
<211> LENGTH: 10
<212> TYPE: PRT
<213> ORGANISM: Homo sapiens

<400> SEQUENCE: 52

Arg Ala Glu Leu Gln Glu Gly Ala Arg Gln
1               5                   10

<210> SEQ ID NO 53
<211> LENGTH: 12
<212> TYPE: PRT
<213> ORGANISM: Homo sapiens

<400> SEQUENCE: 53

Arg Ala Glu Leu Gln Glu Gly Ala Arg Gln Lys Leu
1               5                   10

<210> SEQ ID NO 54
<211> LENGTH: 19
<212> TYPE: PRT
<213> ORGANISM: Homo sapiens

<400> SEQUENCE: 54

Arg Ala Glu Leu Gln Glu Gly Ala Arg Gln Lys Leu His Glu Leu Gln
1               5                   10                  15

Glu Lys Leu

<210> SEQ ID NO 55
<211> LENGTH: 11
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 55

Arg Xaa Lys Leu His Glu Leu Gln Glu Lys Leu
1               5                   10

<210> SEQ ID NO 56
<211> LENGTH: 11
<212> TYPE: PRT
<213> ORGANISM: Homo sapiens
```

-continued

```
<400> SEQUENCE: 56

Arg Gln Lys Leu His Glu Leu Gln Glu Lys Leu
1               5                   10

<210> SEQ ID NO 57
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 57

Arg Xaa Lys Leu His Glu Leu Gln Glu Lys Leu Ser Pro Leu Gly Glu
1               5                   10                  15

Glu Met Arg Asp
            20

<210> SEQ ID NO 58
<211> LENGTH: 20
<212> TYPE: PRT
<213> ORGANISM: Homo sapiens

<400> SEQUENCE: 58

Arg Gln Lys Leu His Glu Leu Gln Glu Lys Leu Ser Pro Leu Gly Glu
1               5                   10                  15

Glu Met Arg Asp
            20

<210> SEQ ID NO 59
<211> LENGTH: 9
<212> TYPE: PRT
<213> ORGANISM: Homo sapiens

<400> SEQUENCE: 59

Lys Leu His Glu Leu Gln Glu Lys Leu
1               5

<210> SEQ ID NO 60
<211> LENGTH: 18
<212> TYPE: PRT
<213> ORGANISM: Homo sapiens

<400> SEQUENCE: 60

Lys Leu His Glu Leu Gln Glu Lys Leu Ser Pro Leu Gly Glu Glu Met
1               5                   10                  15

Arg Asp

<210> SEQ ID NO 61
<211> LENGTH: 20
<212> TYPE: PRT
<213> ORGANISM: Homo sapiens

<400> SEQUENCE: 61

Lys Leu His Glu Leu Gln Glu Lys Leu Ser Pro Leu Gly Glu Glu Met
1               5                   10                  15

Arg Asp Arg Ala
            20

<210> SEQ ID NO 62
<211> LENGTH: 11
<212> TYPE: PRT
<213> ORGANISM: Homo sapiens
```

<400> SEQUENCE: 62

Lys Leu Ser Pro Leu Gly Glu Glu Met Arg Asp
1               5                   10

<210> SEQ ID NO 63
<211> LENGTH: 13
<212> TYPE: PRT
<213> ORGANISM: Homo sapiens

<400> SEQUENCE: 63

Lys Leu Ser Pro Leu Gly Glu Glu Met Arg Asp Arg Ala
1               5                   10

<210> SEQ ID NO 64
<211> LENGTH: 15
<212> TYPE: PRT
<213> ORGANISM: Homo sapiens

<400> SEQUENCE: 64

Lys Leu Ser Pro Leu Gly Glu Glu Met Arg Asp Arg Ala Arg Ala
1               5                   10                  15

<210> SEQ ID NO 65
<211> LENGTH: 13
<212> TYPE: PRT
<213> ORGANISM: Homo sapiens

<400> SEQUENCE: 65

Arg Asp Arg Ala Arg Ala His Val Asp Ala Leu Arg Thr
1               5                   10

<210> SEQ ID NO 66
<211> LENGTH: 11
<212> TYPE: PRT
<213> ORGANISM: Homo sapiens

<400> SEQUENCE: 66

Arg Ala Arg Ala His Val Asp Ala Leu Arg Thr
1               5                   10

<210> SEQ ID NO 67
<211> LENGTH: 22
<212> TYPE: PRT
<213> ORGANISM: Homo sapiens

<400> SEQUENCE: 67

Arg Ala Arg Ala His Val Asp Ala Leu Arg Thr His Leu Ala Pro Tyr
1               5                   10                  15

Ser Asp Glu Leu Arg Gln
            20

<210> SEQ ID NO 68
<211> LENGTH: 20
<212> TYPE: PRT
<213> ORGANISM: Homo sapiens

<400> SEQUENCE: 68

Arg Ala His Val Asp Ala Leu Arg Thr His Leu Ala Pro Tyr Ser Asp
1               5                   10                  15

Glu Leu Arg Gln
            20

<210> SEQ ID NO 69

```
<211> LENGTH: 22
<212> TYPE: PRT
<213> ORGANISM: Homo sapiens

<400> SEQUENCE: 69

Arg Ala His Val Asp Ala Leu Arg Thr His Leu Ala Pro Tyr Ser Asp
1               5                   10                  15

Glu Leu Arg Gln Arg Leu
            20

<210> SEQ ID NO 70
<211> LENGTH: 13
<212> TYPE: PRT
<213> ORGANISM: Homo sapiens

<400> SEQUENCE: 70

Arg Thr His Leu Ala Pro Tyr Ser Asp Glu Leu Arg Gln
1               5                   10

<210> SEQ ID NO 71
<211> LENGTH: 15
<212> TYPE: PRT
<213> ORGANISM: Homo sapiens

<400> SEQUENCE: 71

Arg Thr His Leu Ala Pro Tyr Ser Asp Glu Leu Arg Gln Arg Leu
1               5                   10                  15

<210> SEQ ID NO 72
<211> LENGTH: 19
<212> TYPE: PRT
<213> ORGANISM: Homo sapiens

<400> SEQUENCE: 72

Arg Thr His Leu Ala Pro Tyr Ser Asp Glu Leu Arg Gln Arg Leu Ala
1               5                   10                  15

Ala Arg Leu

<210> SEQ ID NO 73
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 73

Arg Xaa Arg Leu Ala Ala Arg Leu Glu Ala Leu Lys Glu
1               5                   10

<210> SEQ ID NO 74
<211> LENGTH: 13
<212> TYPE: PRT
<213> ORGANISM: Homo sapiens

<400> SEQUENCE: 74

Arg Gln Arg Leu Ala Ala Arg Leu Glu Ala Leu Lys Glu
1               5                   10

<210> SEQ ID NO 75
<211> LENGTH: 11
<212> TYPE: PRT
<213> ORGANISM: Homo sapiens

<400> SEQUENCE: 75
```

Arg Leu Ala Ala Arg Leu Glu Ala Leu Lys Glu
1               5                   10

<210> SEQ ID NO 76
<211> LENGTH: 17
<212> TYPE: PRT
<213> ORGANISM: Homo sapiens

<400> SEQUENCE: 76

Arg Leu Ala Ala Arg Leu Glu Ala Leu Lys Glu Asn Gly Gly Ala Arg
1               5                   10                  15

Leu

<210> SEQ ID NO 77
<211> LENGTH: 13
<212> TYPE: PRT
<213> ORGANISM: Homo sapiens

<400> SEQUENCE: 77

Arg Leu Glu Ala Leu Lys Glu Asn Gly Gly Ala Arg Leu
1               5                   10

<210> SEQ ID NO 78
<211> LENGTH: 20
<212> TYPE: PRT
<213> ORGANISM: Homo sapiens

<400> SEQUENCE: 78

Arg Leu Glu Ala Leu Lys Glu Asn Gly Gly Ala Arg Leu Ala Glu Tyr
1               5                   10                  15

His Ala Lys Ala
            20

<210> SEQ ID NO 79
<211> LENGTH: 15
<212> TYPE: PRT
<213> ORGANISM: Homo sapiens

<400> SEQUENCE: 79

Lys Glu Asn Gly Gly Ala Arg Leu Ala Glu Tyr His Ala Lys Ala
1               5                   10                  15

<210> SEQ ID NO 80
<211> LENGTH: 26
<212> TYPE: PRT
<213> ORGANISM: Homo sapiens

<400> SEQUENCE: 80

Lys Glu Asn Gly Gly Ala Arg Leu Ala Glu Tyr His Ala Lys Ala Thr
1               5                   10                  15

Glu His Leu Ser Thr Leu Ser Glu Lys Ala
            20                  25

<210> SEQ ID NO 81
<211> LENGTH: 9
<212> TYPE: PRT
<213> ORGANISM: Homo sapiens

<400> SEQUENCE: 81

Arg Leu Ala Glu Tyr His Ala Lys Ala
1               5

<210> SEQ ID NO 82

```
<211> LENGTH: 20
<212> TYPE: PRT
<213> ORGANISM: Homo sapiens

<400> SEQUENCE: 82

Arg Leu Ala Glu Tyr His Ala Lys Ala Thr Glu His Leu Ser Thr Leu
1               5                   10                  15
Ser Glu Lys Ala
            20

<210> SEQ ID NO 83
<211> LENGTH: 29
<212> TYPE: PRT
<213> ORGANISM: Homo sapiens

<400> SEQUENCE: 83

Arg Leu Ala Glu Tyr His Ala Lys Ala Thr Glu His Leu Ser Thr Leu
1               5                   10                  15
Ser Glu Lys Ala Lys Pro Ala Leu Glu Asp Leu Arg Gln
            20                  25

<210> SEQ ID NO 84
<211> LENGTH: 13
<212> TYPE: PRT
<213> ORGANISM: Homo sapiens

<400> SEQUENCE: 84

Lys Ala Thr Glu His Leu Ser Thr Leu Ser Glu Lys Ala
1               5                   10

<210> SEQ ID NO 85
<211> LENGTH: 22
<212> TYPE: PRT
<213> ORGANISM: Homo sapiens

<400> SEQUENCE: 85

Lys Ala Thr Glu His Leu Ser Thr Leu Ser Glu Lys Ala Lys Pro Ala
1               5                   10                  15
Leu Glu Asp Leu Arg Gln
            20

<210> SEQ ID NO 86
<211> LENGTH: 33
<212> TYPE: PRT
<213> ORGANISM: Homo sapiens

<400> SEQUENCE: 86

Lys Ala Thr Glu His Leu Ser Thr Leu Ser Glu Lys Ala Lys Pro Ala
1               5                   10                  15
Leu Glu Asp Leu Arg Gln Gly Leu Leu Pro Val Leu Glu Ser Phe Lys
            20                  25                  30
Val

<210> SEQ ID NO 87
<211> LENGTH: 11
<212> TYPE: PRT
<213> ORGANISM: Homo sapiens

<400> SEQUENCE: 87

Lys Ala Lys Pro Ala Leu Glu Asp Leu Arg Gln
1               5                   10

<210> SEQ ID NO 88
```

-continued

```
<211> LENGTH: 22
<212> TYPE: PRT
<213> ORGANISM: Homo sapiens

<400> SEQUENCE: 88

Lys Ala Lys Pro Ala Leu Glu Asp Leu Arg Gln Gly Leu Leu Pro Val
1               5                   10                  15

Leu Glu Ser Phe Lys Val
            20

<210> SEQ ID NO 89
<211> LENGTH: 34
<212> TYPE: PRT
<213> ORGANISM: Homo sapiens

<400> SEQUENCE: 89

Lys Ala Lys Pro Ala Leu Glu Asp Leu Arg Gln Gly Leu Leu Pro Val
1               5                   10                  15

Leu Glu Ser Phe Lys Val Ser Phe Leu Ser Ala Leu Glu Glu Tyr Thr
            20                  25                  30

Lys Lys

<210> SEQ ID NO 90
<211> LENGTH: 13
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 90

Arg Xaa Gly Leu Leu Pro Val Leu Glu Ser Phe Lys Val
1               5                   10

<210> SEQ ID NO 91
<211> LENGTH: 13
<212> TYPE: PRT
<213> ORGANISM: Homo sapiens

<400> SEQUENCE: 91

Arg Gln Gly Leu Leu Pro Val Leu Glu Ser Phe Lys Val
1               5                   10

<210> SEQ ID NO 92
<211> LENGTH: 25
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 92

Arg Xaa Gly Leu Leu Pro Val Leu Glu Ser Phe Lys Val Ser Phe Leu
1               5                   10                  15

Ser Ala Leu Glu Glu Tyr Thr Lys Lys
            20                  25

<210> SEQ ID NO 93
<211> LENGTH: 25
<212> TYPE: PRT
<213> ORGANISM: Homo sapiens

<400> SEQUENCE: 93
```

Arg Gln Gly Leu Leu Pro Val Leu Glu Ser Phe Lys Val Ser Phe Leu
1               5                   10                  15

Ser Ala Leu Glu Glu Tyr Thr Lys Lys
            20                  25

<210> SEQ ID NO 94
<211> LENGTH: 26
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Pyroglutamic acid

<400> SEQUENCE: 94

Arg Xaa Gly Leu Leu Pro Val Leu Glu Ser Phe Lys Val Ser Phe Leu
1               5                   10                  15

Ser Ala Leu Glu Glu Tyr Thr Lys Lys Leu
            20                  25

<210> SEQ ID NO 95
<211> LENGTH: 26
<212> TYPE: PRT
<213> ORGANISM: Homo sapiens

<400> SEQUENCE: 95

Arg Gln Gly Leu Leu Pro Val Leu Glu Ser Phe Lys Val Ser Phe Leu
1               5                   10                  15

Ser Ala Leu Glu Glu Tyr Thr Lys Lys Leu
            20                  25

<210> SEQ ID NO 96
<211> LENGTH: 14
<212> TYPE: PRT
<213> ORGANISM: Homo sapiens

<400> SEQUENCE: 96

Lys Val Ser Phe Leu Ser Ala Leu Glu Glu Tyr Thr Lys Lys
1               5                   10

<210> SEQ ID NO 97
<211> LENGTH: 15
<212> TYPE: PRT
<213> ORGANISM: Homo sapiens

<400> SEQUENCE: 97

Lys Val Ser Phe Leu Ser Ala Leu Glu Glu Tyr Thr Lys Lys Leu
1               5                   10                  15

<210> SEQ ID NO 98
<211> LENGTH: 18
<212> TYPE: PRT
<213> ORGANISM: Homo sapiens

<400> SEQUENCE: 98

Lys Val Ser Phe Leu Ser Ala Leu Glu Glu Tyr Thr Lys Lys Leu Asn
1               5                   10                  15

Thr Gln

OXIDIZED APOA1 DETERMINATION BY MASS SPECTROMETRY

CROSS REFERENCE TO RELATED APPLICATIONS

This application is a divisional of U.S. application Ser. No. 11/489,265, filed Jul. 18, 2006, the entire contents of which are incorporated by reference herein.

FIELD OF THE INVENTION

The present invention relates to methods for detecting and quantitating apolipoprotein A-I and oxidized derivatives thereof, and to the use of this information to assess risk of disease in a subject.

BACKGROUND OF THE INVENTION

The following description of the background of the invention is provided simply to aid in understanding the invention and is not admitted to describe or constitute prior art to the invention.

Apolipoprotein A-I (apoA-I) is the major protein component of the High-Density Lipoprotein (HDL) blood fraction having a nominal concentration of about 1.0 to 1.5 mg/mL in plasma. Mature apoA-I is a single polypeptide chain of 243 amino acids, which maps in humans to gene locus 11q23. ApoA-I is synthesized in the liver and small intestine as a 267-residue preproapolipoprotein. An 18-amino acid residue presequence is cleaved during translation by a signal peptidase, and the resulting proapoA-I contains a hexapeptide prosegment covalently linked to the amino terminus of mature apoA-I. ProapoA-I is secreted into the plasma and lymph and undergoes extracellular posttranslational cleavage of the hexapeptide prosegment to give rise to the mature 243-residue apoA-I.

Multiple properties and functions are ascribed to apoA-I. Specifically, apoA-I is a cofactor for lecithin cholesterol acyltransferase (LCAT), which is responsible for the conversion of cholesterol and phosphatidylcholines (lecithins) to cholesteryl esters and lysophosphatidylcholines on the surface of high density lipoproteins. Hence, apoA-I is implicated in cholesterol metabolism. ApoA-I, as a key element of the reverse cholesterol transport pathway, promotes efflux of cholesterol from cells which include vessel walls. Hence, apoA-I is envisaged to provide a protective mechanism against the development of atherosclerosis. Furthermore, apoA-I is implicated in the organization of HDL structure.

A correlation between the occurrence of cardiovascular disease (CVD), and in particular atherosclerotic heart disease, and oxidative processes is long known in the art. See e.g., Chisolm & Steinberg (2000) *Free Radic. Biol. Med.* 28:1815-1826; Navab et al. (2002) *Curr. Opin. Lipidol.* 13:363-372; Ross (2003) *New Engl. J. Med.* 340:115-126; and Heinecke (2003) *Am. J. Cardiol.* 91:12A-16A. For example, the extent of modification of apoA-I by oxidation of tyrosine (i.e., chlorination and nitration) is correlated with functional impairment in reverse cholesterol transport activity of isolated apoA-I [Zheng et al. (2004) *J. Clin. Investig.* 114:529-541.]

Further investigation (e.g., Zheng et al. (2004) *J. Clin. Investig.* 114:529-541) has demonstrated that apoA-I is a selective target for nitration and chlorination in vivo by myeloperoxidase (MPO, EC 1.11.1.7). MPO is a heme-containing protein that maps to human gene locus 17q23.1, which is synthesized by various phagocytes. Although produced as a single chain precursor of 80-kD, MPO is subsequently cleaved into light (12-kD) and heavy (60-kD) chains, which form mature MPO, a tetramer composed of 2 light chains and 2 heavy chains. MPO utilizes hydrogen peroxide and chloride to generate chlorinating oxidants, e.g., HOCl, that kill pathogens. Additionally, in human monocytes, MPO utilizes hydrogen peroxide and nitrite to generate nitrating oxidants capable of lipid and protein nitration. A correlation has been established between plasma MPO levels and the incidence of myocardial infarction in patients presenting with chest pain (Brennan et al. (2003) *New Engl. J. Med.* 349: 1595-1604).

Further elucidation of the role of MPO-mediated oxidation of apoA-I has been provided by various investigators (e.g., Zheng et al., *J. Biol. Chem.* (2005) 280:38-47) which identified the sites of MPO-mediated oxidation of apoA-I in vitro and in vivo as $Tyr^{192}$, $Tyr^{166}$, $Tyr^{236}$, and $Tyr^{29}$ (SEQ ID NO: 2). Site-specific quantitative analyses conducted by these investigators demonstrate that the favored modification site within apoA-I after exposure to MPO-generated oxidants is $Tyr^{192}$, with $Tyr^{166}$ oxidized as a secondary site, and with $Tyr^{236}$ and $Tyr^{29}$ modified only minimally. The term "favored modification site" refers to the apoA-I amino acid which is oxidized to the greatest extent after exposure to MPO-generated oxidants. The term "secondary site" refers to an apoA-I amino acid which may be oxidized after exposure to MPO-generated oxidants, but for which the frequency of oxidation is not as great as for a favored modification site. The term "minimally" in this context refers to amino acid sites of apoA-I which undergo a low frequency of oxidation by MPO-generated oxidants under physiological conditions.

SUMMARY OF THE INVENTION

The present invention provides methods for the rapid and efficient determination of the oxidation status of apoA-I of a biological sample by determining the extent of oxidation of amino acid residues thereof. Additionally, there are provided methods for the assessment of the risk of CVD in a subject based on the oxidation status of apoA-I as determined herein.

In a first aspect, the invention provides a method for determining the oxidation status of apoA-I which method includes either a) comparing the total amount of apoA-I having at least one oxidized amino acid residue with the total amount of apoA-I, or b) comparing the total amount of at least one target fragment of apoA-I having at least one oxidized amino acid residue with the total amount of the apoA-I target fragment. The term "oxidation status" refers to a metric of the extent to which specific amino acid residues are replaced by corresponding oxidized amino acid residues in a target protein or a target fragment. The term "extent of oxidation" refers to the degree to which potentially oxidizable amino acids in a target protein or target fragment have undergone oxidation. For example, if the target fragment contains a single tyrosine residue which is potentially oxidized to 3-chlorotyrosine, then an increase in mass of about 34 Dalton (i.e., the approximate difference in mass between chlorine and hydrogen) indicates oxidation of tyrosine to 3-chlorotyrosine. Oxidation status can be measured by metrics known to the arts of protein and peptide chemistry including, without limitation, assay of the number of oxidized residues, mass spectral peak intensity, mass spectral integrated area, and the like. In some embodiments of any of the aspects provided herein, oxidation status is reported as a percentage, wherein 0% refers to no oxidation and 100% refers to complete oxidation of potentially oxidizable amino acid residues within apoA-I or target fragment. The term "potentially subject to oxidation," "potentially oxidizable amino acid residues", and the like refer to an amino acid which can undergo oxidation, for example by nitration or chlorination. In the context of the present invention, the term "target protein" refers to apoA-I. The term "target fragment" refers to a polypeptide comprising a sequence of amino acid residues, which sequence is contained within the target protein (i.e., apoA-I).

In another aspect, the invention provides a method for quantitating the amount of oxidized apoA-I from a biological sample. The method includes determining the oxidation fraction of apoA-I from the biological sample; determining the total amount of apoA-I from a biological sample; and multiplying the total amount of apoA-I by the oxidation fraction. The term "oxidation fraction" refers to the term "oxidation status" as defined herein expressed as a fraction in the range 0-1, e.g., 0.0, 0.1, 0.2, 0.3, and the like up to 1.0. It is understood that the number of significant digits in an oxidation status, oxidation fraction, or other experimental result herein is a function of the sensitivity of the instruments and experimental protocols and can assume values of 1, 2, 3, 4, or even more significant digits. Methods for the calculation of significant digits are well known in the art. The phrase "determining the oxidation fraction" refers to determining the oxidation status, as defined herein, and expressing the result as a fraction of amino acids of the target protein which can be replaced by corresponding oxidized amino acid residues. The term "total amount of target protein in a biological sample" and like terms refer to the total amount of target protein irrespective of the oxidation state of the constituent amino acids thereof. In some embodiments of this aspect, the total amount of apoA-I is determined by assay, for example without limitation, a standard immunoassay well known in the art. Examples of reagents readily available for immunometric determination of apoA-I include antiserum to apoA-I (Dade Behring, Deerfield, Ill.). In some embodiments of this aspect, the total amount of apoA-I is multiplied by the oxidation fraction to provide a quantitation of the amount of oxidized apoA-I in a biological sample. For example without limitation, if the oxidation fraction were 0.5 and the total concentration of apoA-I in the biological sample were 1.0 mg/mL, the amount of oxidized apoA-I in the biological sample would be reported as 0.5 mg/mL (i.e., 0.5×1.0 mg/mL).

In another aspect, the oxidation status of apoA-I in a biological sample is correlated with the risk of CVD in order to provide an assessment of the risk thereof by the subject from which the biological sample was obtained. In some embodiments of this aspect, the oxidation status of apoA-I in a biological sample of a subject is determined by methods described herein, and the resulting oxidation status is used with a standard curve that relates oxidation status to risk of CVD.

In some embodiments of this aspect, the determination of the oxidation status of apoA-I in a biological sample of a subject includes the steps of a) determining the mass and amount of apoA-I in a biological sample; b) comparing the mass determined for the apoA-I with the mass of apoA-I which is not oxidized, wherein an increase in mass of apoA-I over the mass of the apoA-I which is not oxidized reflects the number of oxidized amino acid residues in the apoA-I; and c) determining the oxidation status of apoA-I from the total amount of apoA-I having at least one oxidized amino acid residue and the total amount of apoA-I. In some alternative embodiments of this aspect, the determination of the oxidation status of apoA-I in a biological sample of a subject includes the steps of d) determining the mass and amount of at least one target fragment obtained by fragmentation of apoA-I, wherein the at least one target fragment contains at least one amino acid residue potentially subject to oxidation; e) comparing the mass determined for the at least one target fragment with the mass of the same target fragment from apoA-I which is not oxidized, wherein an increase in mass of the at least one target fragment over the mass of the same target fragment from apoA-I which is not oxidized reflects the number of oxidized amino acid residues in the at least one target fragment; and t) determining the oxidation status of apoA-I from the total amount of the at least one target fragment having at least one oxidized amino acid residue and the total amount of the at least one target fragment.

The term "subject" refers to a mammal having a blood fraction comprising HDL and/or LDL. In some embodiments of any of the above aspects, the oxidation status of apoA-I in a biological sample obtained from the subject is determined by determining the mass and amount of at least one target fragment obtained by fragmentation of the apoA-I, wherein the at least one target fragment contains at least one amino acid residue potentially subject to oxidation; comparing the mass determined for the at least one target fragment so obtained with the mass of the same target fragment from apoA-I which is not oxidized, wherein an increase in mass of the at least one target fragment over the mass of the same target fragment from apoA-I which is not oxidized reflects the number of oxidized amino acid residues in the at least one target fragment; and determining the oxidation status of apoA-I from the total amount of the at least one target fragment having at least one oxidized amino acid residue and the total amount of the at least one target. Risk of CVD is assessed by inspection of the oxidation status in view of the correlation of CVD with oxidation of apoA-I. For example, no oxidation of apoA-I (i.e., ratio of oxidized/total apoA-I=0) implies no excess risk of CVD correlated to oxidized apoA-I. Alternatively, complete oxidation of apoA-I (i.e., ratio of oxidized/total apoA-I=1) implies the greatest risk of CVD correlated to oxidized apoA-I. In this context, the term "excess risk" refers to the potential for CVD attributable to the oxidation state of the apoA-I. Evaluation of the excess risk due to oxidized apoA-I can be determined for example by methods known in the field of epidemiology using, for example, the reported correlation between the occurrence of CVD and oxidative processes. See e.g., Chisolm & Steinberg (2000) *Free Radic. Biol. Med.* 28:1815-1826; Navab et al. (2002) *Curr. Opin. Lipidol.* 13:363-372; Ross (2003) *New Engl. J. Med.* 340: 115-126; and Heinecke (2003) *Am. J. Cardiol.* 91:12A-16A.

In some embodiments of any of the above aspects, the apoA-I is obtained from a biological sample. The term "biological sample" refers to explanted, withdrawn or otherwise collected biological tissue or fluid including, for example without limitation, whole blood, serum and plasma. The term "serum" in the context of blood refers to the fluid obtained upon separating whole blood into solid and liquid components after it has been allowed to clot. In some embodiments of any of the above aspects, the biological sample is of human origin. In some embodiments of any of the above aspects, the biological sample is serum. In some embodiments of any of the above aspects, the biological sample is plasma.

In some embodiments of any of the above aspects, the method further includes affinity purification of apoA-I. In some embodiments of any of the above aspects, the method includes determining the mass of apoA-I or target fragment by mass spectrometry. In some embodiments of any of the above aspects, the method includes determining the mass of apoA-I or target fragment by MS/MS spectrometry.

In some embodiments of any of the above aspects, apoA-I may be fragmented into target fragments, and the mass and amount of at least one target fragment which contains amino acid residues potentially subject to oxidation is measured.

In some embodiments of any of the above aspects, the invention provides for comparison of the mass of at least one target fragment obtained from apoA-I with the mass of the same target fragment (i.e., a polypeptide having the same amino acid residue sequence and amino and carboxyl terminii) from apoA-I which is not oxidized. The terms "same target protein which is not oxidized," "apoA-I which is not oxidized," and the like refer to apoA-I which has not undergone posttranslational oxidation. The increase in mass of a target fragment over the mass of the same target fragment from apoA-I which is not oxidized reflects the number of oxidized amino acid residues in the target fragment. The increase in amount of target fragment having oxidized residues over the amount of target fragment which has no oxidized residues reflects the extent of oxidation. Then, the oxidation status of apoA-I is determined from the total amount of target apoA-I having one or more oxidized amino acid residues and the total amount of target fragment.

In some embodiments of any of the above aspects, apoA-I is not fragmented. In some embodiments of aspects which contemplate determining the oxidation status of apoA-I, the determination comprises comparing the total amount of apoA-I having at least one oxidized amino acid residue with the total amount of apoA-I.

In some embodiments of any of the above aspects, oxidation of apoA-I is manifest as chlorination and/or nitration. In some embodiments of any of the above aspects, the amino acid residue is tyrosine, and the corresponding oxidized amino acids are 3-chlorotyrosine and 3-nitrotyrosine. In some embodiments of any of the above aspects, oxidation status is determined by direct measurement of the abundance of oxidized amino acid residues with respect to unmodified amino acid residues in at least one target fragment of apoA-I. In some embodiments of any of the above aspects, the unmodified amino acid residue in the target fragment(s) is tyrosine, and the corresponding oxidized amino acid residues are 3-chlorotyrosine and 3-nitrotyrosine. Accordingly, complete oxidation of all tyrosine to either 3-chlorotyrosine or 3-nitrotyrosine corresponds to an oxidation status of 100% for apoA-I. In some embodiments of any of the above aspects, a representative subset of tyrosine residues within apoA-I is selected to represent the oxidation status. Within the context of embodiments of the present invention contemplating tyrosine as a representative subset, complete oxidation of the representative set of tyrosine residues represents an oxidation status of 100%. In some embodiments of any of the above aspects, the subset of tyrosine residues selected to represent the oxidation status consists of all tyrosines within apoA-I (SEQ ID NO: 2). In some embodiments of any of the above aspects, the subset of tyrosine residues selected to represent the oxidation status consists of apoA-I $Tyr^{92}$ (SEQ ID NOs: 78, 79, 80, 81, 82, and 83). Accordingly, in this context complete oxidation of $Tyr^{192}$ (SEQ ID NOs: 78, 79, 80, 81, 82, and 83) corresponds to an oxidation status of 100% for apoA-I. In some embodiments of any of the above aspects, the mass and amount of a single target fragment having a potentially oxidizable amino acid are determined in order to calculate the oxidation status of apoA-I originally containing the target fragment. In some embodiments of any of the above aspects, the masses and amounts of a plurality of distinct target fragments having potentially oxidizable amino acid residues are used to determine the oxidation status of apoA-I. In some embodiments of any of the above aspects where a plurality of target fragments are analyzed, the oxidation status of apoA-I can be calculated from the total amount of target fragments having an oxidized amino acid residue and the total amount of target fragments. In some embodiments of any of the above aspects where a plurality of target fragments are analyzed, the oxidation status of apoA-I can be calculated as the arithmetic mean of the oxidation statuses of the individual target fragments that form the plurality. The term "oxidation status of the individual target fragments" refers to the oxidation status calculated for distinct target fragments by neglecting the oxidation status of any other target fragment. In some embodiments of any of the above aspects, the oxidation status of apoA-I can be calculated as the weighted mean of the oxidation statuses of the individual target fragments, wherein the term "weighted" refers to a statistical weight as is well known in the art. Example weights include without limitation weights proportional to the total amount of the distinct target fragment for which each oxidation status is determined, and weights proportional to the occurrence of specific oxidized amino acids in apoA-I as found in a plurality of subjects using epidemiological methods well known in the art. The term "about" when used in the context of a number means the number plus or minus 10%.

In some embodiments of any of the above aspects, fragmentation of apoA-I into target fragments can be achieved by a variety of techniques known in the art, including without limitation, dissociation within a mass spectrometer, chemical cleavage, and proteolytic cleavage. The terms "fragmentation," "fragmenting," and the like refer to the result of specific cleavage of a polypeptide or protein (e.g., the target protein) backbone. In some embodiments of any of the above aspects, fragmentation of apoA-I into target fragments comprises proteolytic digestion. The terms "reaction with a protease," "proteolytic digestion," and the like refer to the methodology of proteolytic digestion by the use of one or more proteases. Proteases contemplated by the invention include, without limitation, serine proteases, e.g., trypsin, chymotrypsin, elastase, and the like; sulfhydryl proteases, e.g., papain, ficin, and the like; acid proteases, e.g., pepsin and the like; and metalloproteases, e.g., thermolysin, carboxypeptidase A or B, matrix metalloprotease, and the like. In some embodiments of any of the above aspects, the protease employed in the proteolytic digestion step is trypsin.

In some embodiments of any of the above aspects, apoA-I is enriched prior to fragmentation into target fragments. The terms "enriching," "enrichment," and the like refer to purification, i.e., an increase in relative concentration by any one or more methods known in the art of biochemical purification. Accordingly, "enrichment of the target protein," "enrichment of apoA-I," and like terms refer to the process whereby the concentration of apoA-I is increased relative to the concentrations of other constituents of the biological sample. The term "other constituents of the biological sample" and like terms refer to components of the biological sample which are not apoA-I. Examples of such other constituents include, without limitation, immunoglobulins and albumins. Such methods of enrichment include, for example without limitation, removal of blood cells and blood cell components, removal of other constituents of the biological sample, affinity purification of apoA-I, precipitation, differential solubility as a function of ionic strength, pH, and temperature, and the like. The term "blood cell components" refers to proteins and lipoproteins found in blood, examples of which include without limitation, immunoglobulins, coagulation and complement factors, and the like. In some embodiments of any of the above aspects, precipitation includes reaction with polyanions, for example without limitation, dextran sulfate, phosphotungstate, or the like, in the presence of divalent cations such as calcium, magnesium, manganese, or the like by methods well known in the art. In some embodiments of any of the above aspects, the enrichment comprises affinity purification. In some embodiments of any of the above aspects, the affinity purification includes the steps of incubating the biological sample containing apoA-I with an affinity reagent such that apoA-I complexes with the affinity reagent, and subsequently removing non-binding materials from the complex of apoA-I and affinity reagent. In some embodiments of any of the above aspects, the affinity reagent is an antibody. In some embodiments of any of the above aspects, the affinity reagent is an aptamer. In some embodiments of any of the above aspects, following removal of non-binding materials, the complex of apoA-I and affinity reagent is separated into apoA-I and affinity reagent components, thereby increasing the concentration of apoA-I relative to the concentration of other proteins in the biological sample.

In some embodiments of any of the above aspects, enrichment of apoA-I comprises removal from the biological sample of other constituents thereof. For example, removal of blood cell components of the biological sample by methods long known in the art results in purification of apoA-I by the removal of protein and lipoprotein components of the blood cells. In some embodiments of any of the above aspects, enrichment of apoA-I comprises removal from the biological sample of other constituents including, for example without limitation, immunoglobulins and albumin.

In some embodiments of any of the above aspects, enrichment of apoA-I includes affinity purification and occurs via differential interaction of the target protein with an affinity matrix to form a complex, and subsequent removal of unbound (i.e., uncomplexed) materials from the apoA-I affinity reagent complex. In some embodiments of any of the above aspects, the compound(s) of the affinity matrix are further separated from apoA-I, while in yet other embodiments, apoA-I is retained with one or more compositions of the affinity matrix.

DETAILED DESCRIPTION OF THE INVENTION

In some embodiments of any of the above aspects, apoA-I is fragmented into target fragments. Target fragments can comprise any length of polypeptide comprising a contiguous subset of amino acid residues of apoA-I from one amino acid residue up to the length of apoA-I, e.g., 1, 2, 3, 4, 5, 6, 7, 8, 9, 10, 12, 14, 16, 18, 20, or more amino acid residues. Target fragments can be identified by a variety of methods known in the biochemical arts, including, for example without limitation, direct sequencing, comparison of chromatographic behavior with standard polypeptides, and mass spectrometry. In some embodiments of any of the above aspects, target fragment sequences can be deduced based on the specificity of proteases used in proteolytic fragmentation of apoA-I by methods well known in the art. In some embodiments of any of the above aspects, identification of target fragments is by mass spectrometry.

Regarding trypsin catalyzed cleavage, trypsin specificity, being to the C-terminal of arginine and lysine residues, results in fragments containing these highly basic residues at the C-terminal. The presence of C-terminal basic residues has been found to facilitate interpretation of MS/MS spectra [Olsen et al. (2004) *Molecular & Cellular Proteomics* 3:608-614]. Factors which influence the extent to which trypsin proteolytic digestion proceeds include time of incubation, solution conditions including pH, temperature, ionic strength, and other factors well known in the art, as well as residual secondary and tertiary structure of the trypsin substrate during digestion. A biological sample containing apoA-I can be incubated with trypsin for a defined time period, for example without limitation, 1, 5, 10, 15, 30, 45 minutes, 1, 2, 3, 4, 8, 12 hours, overnight, 1 day, or even longer. The temperature can be room temperature, or any other temperature wherein trypsin is active as a protease of apoA-I, for example without limitation, 4, 8, 12, 16, 20, 25, 30, 32, 34, 36, 37, 38, 40, 45, 50, 60 degrees Celcius, or even higher. In some embodiments of any of the above aspects, proteolytic digestion results in all potential cleavage sites being cleaved; i.e., exhaustive proteolytic digestion.

The term "potential cleavage site" refers to a peptide bond which is known to be susceptible to cleavage by a protease, for example, by virtue of sequence. In some embodiments, proteolytic digestion is limited by time and/or solution conditions well known in the art such that certain potential cleavage sites are not cleaved. Accordingly, the resulting target fragments may contain internal (i.e., neither C-terminal nor N-terminal) potential cleavage sites and comprise more residues than target fragments obtained after exhaustive proteolytic digestion.

In some embodiments of any of the above aspects, determination of the mass of target fragments employs mass spectrometry. The terms "mass spectrometry," "MS." and the like refer to methods of filtering, detecting, and measuring ions based on their mass-to-charge (i.e., "m/z") ratio. The terms "mass" and "m/z" are used interchangeably within the context of the results of mass spectrometric analysis, and unless otherwise indicated, all m/z values assume singly ionized species. The terms "main isotope mass" and "main isotope m/z" refer to the mass reported for a molecular ion taking into account the mass of the most abundant (i.e., main) isotope of each element. In general, one or more molecules of interest are ionized, and the ions are subsequently introduced into a mass spectrometer where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000), each of which is hereby incorporated by reference in its entirety and for all purposes, including all tables, figures, and claims. The terms "integrated intensity," "mass spectral integrated area," "integrated mass spectral intensity," and the like refer to the area under a mass spectrometric curve corresponding to the amount of a molecular ion having a particular main isotope m/z, as is well known in the art.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Moreover, one can often enhance the resolution of the MS technique by employing "tandem mass spectrometry," or "MS/MS." In this technique, a first, or parent, ion generated from a molecule of interest can be filtered in an MS instrument, and these parent ions subsequently fragmented to yield one or more second, or daughter, ions that are then analyzed in a second MS procedure. By careful selection of parent ions, only ions produced by certain analytes are passed to the fragmentation chamber, where collision with atoms of an inert gas to produce these daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS"." Various other combinations may be employed, such as MS/MS/TOF, MALDI/MS/MS/TOF, or SELDI/MS/MS/TOF mass spectrometry.

Ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

The term "electron ionization" refers to methods in which an analyte of interest in a gaseous or vapor phase is interacted with a flow of electrons. Impact of the electrons with the analyte produces analyte ions, which may then be subjected to a mass spectroscopy technique.

The term "chemical ionization" refers to methods in which a reagent gas (e.g. ammonia) is subjected to electron impact, and analyte ions are formed by the interaction of reagent gas ions and analyte molecules.

The term "fast atom bombardment" refers to methods in which a beam of high energy atoms (often Xe or Ar) impacts a non-volatile test sample, desorbing and ionizing molecules contained in the sample. Samples are dissolved in a viscous liquid matrix, such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "field desorption" refers to methods in which a non-volatile test sample is placed on an ionization surface, and an intense electric field is used to generate analyte ions.

The term "maxtrix-assisted laser desorption ionization," or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

The term "surface enhanced laser desorption ionization," or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization" or ESI refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," refers to methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "inductively coupled plasma" refers to methods in which a sample is interacted with a partially ionized gas at a sufficiently high temperature to atomize and ionize most elements.

The term "ionization" refers to the process of generating an analyte ion having a net electrical charge equal to one or more charge units. The term "charge unit" refers in the usual sense to the fundamental electrical charge of a proton. Negative ions are those ions having a net negative charge of one or more charge units, while positive ions are those ions having a net positive charge of one or more charge units.

The term "operating in negative ion mode" refers to those mass spectrometry methods where negative ions are detected. Similarly, "operating in positive ion mode" refers to those mass spectrometry methods where positive ions are detected.

The term "desorption" refers to the removal of an analyte from a surface and/or the entry of an analyte into a gaseous phase.

In those embodiments, such as MS/MS, where parent ions are isolated for further fragmentation, collision-induced dissociation (i.e., "CID") is often used to generate the ion fragments for further detection. In CID, parent ions gain energy through collisions with an inert gas, and subsequently fragment by a process referred to as "unimolecular decomposition." Sufficient energy must be deposited in the parent ion so that certain bonds within the ion can be broken due to increased vibrational energy.

In exemplary embodiments described herein, the mass of apoA-I, at least one target fragment or the masses of a plurality of target fragments of apoA-I, are determined. Oxidation of amino acid residues by for example chlorination or nitration results in modified amino acid residues with characteristic masses. As shown in Chart I below, tyrosine, 3-chlorotyrosine, and 3-nitrotyrosine have nominal (i.e., uncharged) main isotope masses of 181.07, 215.03, and 226.06 Dalton, respectively. Accordingly, target fragments which comprise 3-chlorotyrosine or 3-nitrotyrosine have masses of approximately 34.0 or 45.0 Dalton (i.e., main isotopic mass) respectively, in excess of the mass of the corresponding target fragment without oxidized tyrosine. It is well understood in the art that observed mass, for example as determined by mass spectrometry, have an inherent error, which error can be +/−1, 2, 3, 4, 5, or more Dalton, and which error can be a percentage, e.g., +/−0.1%, 0.5%, 1.0%, 2.0%, 3.0%, 4.0%, 5.0%, 10.0%, or even larger.

Chart I

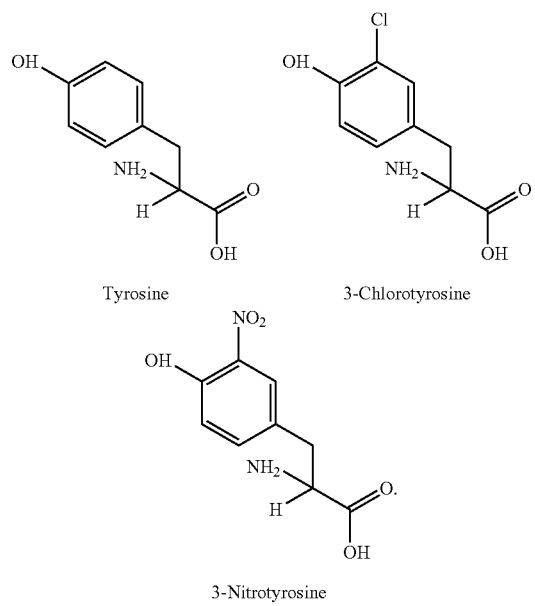

Tyrosine  3-Chlorotyrosine

3-Nitrotyrosine

In some embodiments of any of the above aspects, a sample containing target fragments is subjected to mass spectrometric analysis thereby providing a mass spectrum comprising all (i.e., unoxidized, partially oxidized, and fully oxidized) fragments within the sample. Accordingly, target fragments comprising any of the seven tyrosine residues naturally occurring within apoA-I (i.e., at positions 18, 29, 100, 115, 166, 192, and 236 of SEQ ID NO: 2) are subject to excess mass due to oxidation of tyrosine. Comparison of the amount of unoxidized and oxidized tyrosine in target fragments, as measured, for example without limitation, by the integrated mass spectral intensity of the corresponding mass spectral peak of target fragments containing unoxidized tyrosine, 3-chlorotyrosine, or 3-nitrotyrosine, provides the amount of target fragments having oxidized tyrosine as well as the amount of fragments having no oxidized tyrosine. In some embodiments of any of the above aspects, the amount and mass of each target fragment are determined by the intensity and position, respectively, of mass spectral peaks as determined by mass spectrometry. In some embodiments of any of the above aspects, the amount and mass of each target fragment are determined by the integrated intensity and position, respectively, of mass spectral peaks as determined by mass spectrometry.

In some embodiments of any of the above aspects, the amount of each target fragment in each possible oxidation state is determined by comparison of the amount of oxidized and unoxidized amino acid residues. The amount of each target fragment in each possible oxidation state can be determined, for example, by the integrated intensity of the peaks corresponding to the mass of each target fragment in each possible oxidation state as determined by mass spectrometry.

In some embodiments of any of the above aspects, the comparison of unoxidized and oxidized amino acid residues within target fragments may be determined by evaluating unoxidized and oxidized tyrosine. In some embodiments of any of the above aspects, the comparison is directed at specific tyrosine residues, for example tyrosine at positions 18, 29, 100, 115, 166, 192, and 236 of apoA-I (SEQ ID NO: 2). In some embodiments of any of the above aspects, the comparison is directed at $Tyr^{166}$ and $Tyr^{192}$ of apoA-I (SEQ ID NO: 2). In some embodiments of any of the above aspects, the comparison is directed at $Tyr^{192}$ of apoA-I (SEQ ID NOs: 2, 78-83).

The comparison of the amount of target fragments having oxidized or unoxidized amino acid residues provides a metric of the number of oxidized amino acid residues in at least one target fragment of apoA-I. In some embodiments of any of the above aspects, the ratio of the amount of target fragment having at least one oxidized amino acid residue to the total amount of target fragment having amino acids potentially subject to oxidation determines the oxidation status of apoA-I. In some embodiments of any of the above aspects, the amino acid is a tyrosine of apoA-I (SEQ ID NO: 2).

In some embodiments of any of the above aspects, enrichment of apoA-I includes affinity purification directed to other components of the biological sample, whereby differential interaction of one or more other constituents of the biological sample with an affinity matrix results in a complex, and subsequent removal of the complex results in enrichment of apoA-I.

The term "affinity matrix" refers to any one or more affinity compositions which differentially react with apoA-I or other constituents of the biological sample such that subsequent biochemical purification results in separation of apoA-I from other components of the biological sample. In this context, the term "differentially react" refers to the formation of a complex between apoA-I or other constituents of the biological sample and affinity matrix. In some embodiments, the complex of apoA-I or other constituents of the biological sample with affinity matrix is maintained by non-covalent forces. In additional embodiments, one or more covalent bonds are formed between apoA-I or other constituents of the biological sample and affinity matrix. Affinity matrices includes antibodies, aptamers, and immobilized derivatives thereof. In some embodiments, the affinity matrix is an aptamer. In some embodiments, the affinity matrix is an antibody.

The term "aptamer" refers to macromolecules composed of nucleic acid, such as RNA or DNA, that bind tightly to a specific molecular target. The terms "bind," "binding" and the like refer to an interaction or complexation resulting in a complex sufficiently stable so as to permit separation. In some embodiments, the aptamer specifically binds apoA-I. Methods for the production and screening of aptamers useful for the present invention are well known in the art; see e.g., Griffin et al., U.S. Pat. No. 5,756,291 entitled "Aptamers Specific for Biomolecules and Methods of Making," incorporated herein by reference in its entirety and for all purposes.

As usually practiced in the art, the method of selection (i.e., training) of aptamer requires a pool of single stranded random DNA oligomers comprising both random sequences and flanking regions of known sequence to serve as primer binding sites for subsequent polymerase chain reaction (PCR) amplification. Such DNA oligomers are generated using conventional synthetic methods well known in the art. As an initial and optional step, PCR amplification is conducted by conventional methods, and the amplified pool is left as duplex DNA, or used as single stranded DNA after strand separation. Optionally, transcription into RNA can be conducted. The term "oligomer pool" in this context refers to such single stranded or duplex DNA, or RNA transcribed therefrom. The term "refined oligomer pool" refers to an oligomer pool which has been subjected to at least one round of selection as described herein.

Further the aforementioned aptamer training, a "selection" step is conducted employing a column or other support matrix (i.e., target-coupled support) having target molecule attached thereon. Attachment, well known in the art, may be by covalent or non-covalent means. The oligomer pool, or refined oligomer pool, and target-coupled support are incubated in order to permit formation of oligonucleotide-target complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for target relative to a predecessor oligomer pool or refined oligomer pool.

Alternatively, the aforementioned aptamer training can employ a "reverse selection" step wherein aptamer is selected to bind to other constituents of the biological sample. In this case, a column or other support matrix is employed (i.e., constituent-coupled support) having other constituents of the biological sample attached thereon. The oligomer pool, or refined oligomer pool, and constituent-coupled support are incubated in order to permit formation of oligonucleotide-constituent complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for other constituents of the biological sample relative to a predecessor oligomer pool or refined oligomer pool. Examples of other constituents of the biological sample used in the reverse selection step include, without limitation, immunoglobulins and albumins.

In a typical production training scheme, oligonucleotide recovered after complexation with target or other constituent of the biological sample is subjected to PCR amplification. The selection/amplification steps are then repeated, typically three to six times, in order to provide refined oligomer pools with enhanced binding and specificity to target or other constituent of the biological sample. Amplified sequences so obtained can be cloned and sequenced. Optionally, when a plurality of individual aptamer sequence specific for a target having been obtained and sequenced, pairwise and multiple alignment examination, well known in the art, can result in the elucidation of "consensus sequences" wherein a nucleotide sequence or region of optionally contiguous nucleotides are identified, the presence of which correlates with aptamer binding to target. When a consensus sequence is identified, oligonucleotides that contain the consensus sequence may be made by conventional synthetic or recombinant means.

The term "antibody" refers to an immunoglobulin which binds antigen (i.e., target protein, target fragment, or other component of the biological sample) with high affinity and high specificity. In this context "high affinity" refers to a dissociation constant of, for example without limitation, 1 µM, 100 nM, 10 nM, 1 nM, 100 pM 10 pM, 1 pM, or even more, characterizing the binding reaction of antibody with antigen to which the antibody has been raised. The term "raised" refers to the production of high affinity antibody by methods long known in the art. Further in this context, the term "high specificity" refers to a preference of binding of antigen by a test antibody relative to non-antigen characterized by a ratio of dissociation constants of, for example without limitation, 1, 2, 5, 10, 20, 50, 100, 200, 500, 1000, 10000, or more, in favor of binding of antigen to which the test antibody has been raised.

Methods of derivatization of antibodies and aptamers contemplated by the present invention include, for example without limitation, biotinylation. In some embodiments, the antibody or aptamer is biotinylated such that subsequent isolation on an avidin conjugated matrix, for example without limitation, an avidin chromatography column, affords facile separation by methods well known in the art of biochemical purification. In some embodiments, the biotinylated antibody or aptamer in complex with apoA-I is further subjected to streptavidin-conjugated magnetic beads. The ternary apoA-I-biotinylated affinity reagent-streptavidin conjugated magnetic bead complex is then isolated by immunomagnetic methods well known in the art.

In some embodiments, the biological sample is incubated with an affinity reagent under conditions such that a complex is formed between apoA-I and the affinity reagent, and in a subsequent step the complex so formed is selected (i.e., isolated) thereby enriching apoA-I.

In some embodiments of any of the aspect provided herein, at least one target fragment resulting from a fragmentation step is enriched prior to the determination of the mass of at least one of the target fragments. Enrichment of at least one target fragment can employ methods well known in the art including, without limitation, chromatography and affinity purification. In some embodiments, enrichment of at least one target fragment is by chromatography on, for example without limitation, a $C_{18}$ column as routinely employed in the art.

In some embodiments of any of the above aspects, the method further comprises determining the mass and amount of all target fragments from apoA-I which contain amino acid residues potentially subject to oxidation; comparing the masses determined for all target fragment with the masses of the same target fragments from apoA-I which are not oxidized, wherein an increase in mass of all target fragments of apoA-I over the masses of the same target fragments from apoA-I which are not oxidized reflects the number of oxidized amino acid residues in all target fragments; and determining the oxidation status of apoA-I from the total amount of oxidized amino acid residues of all target fragments of apoA-I and the total amount of all target fragments.

EXAMPLES

Examples related to the present invention are described below. In most cases, alternative techniques could also be used. The examples are intended to be illustrative and are not limiting or restrictive to the scope of the invention.

Example 1

Biological Sample Preparation

Serum can be obtained from a subject by taking a blood sample (i.e., biological sample) and allowing the blood sample to clot, using methods of sterile sample collection and storage well known in the art. The clotted sample is then centrifuged and the serum (i.e. supernatant) is retained for subsequent manipulation.

Partial purification of target protein apoA-I can be afforded from the initial biological sample by the facile removal of albumin and immunoglobulin G (IgG) using, for example, the ProteoPrep Albumin Deletion Kit (Sigma-Aldrich, Saint Louis, Mo.) via a simple column chromatographic step wherein target protein flows through but albumin and immunoglobulin G is retained, as well known in the art.

Example 2

Affinity Purification

A.1. —Antibody Production

Production of antibody to apoA-I, or fragments thereof, can employ methods routinely used in the art of antibody production. For example, unoxidized apoA-I can serve as immunization agent for the production of anti-(unoxidized)-apoA-I in an immunocompetent animal for example, without limitation, rabbit, goat, sheep, horse, and the like. The term "immunocompetent" refers to the ability to produce antibody. In this context, the term "unoxidized apoA-I" refers to apoA-I which contains no 3-chlorotyrosine or 3-nitrotyrosine. The term "anti-(unoxidized)-apoA-I" refers to antibody produced using unoxidized apoA-I as immunogen. Generally speaking, the antibody produced thereby is polyclonal and can react in principle with multiple determinants of apoA-I, and with apoA-I in multiple states of oxidation as measured by the presence of 3-chlorotyrosine and/or 3-nitrotyrosine at any one or more of the seven naturally occurring tyrosine residue positions in apoA-I.

In order to refine the spectrum of determinants to which anti-apoA-I reacts, a immunochromatographic step can be employed one or more times which selectively removes or retains antibody with specificity to either oxidized or unoxidized apoA-I. For example, anti-(unoxidized)-apoA-I can be applied to a column to which oxidized apoA-I has been covalently affixed using methods well known in the art, for example without limitation, crosslinking to Sepharose with glutaraldehyde. In this context, "oxidized apoA-I" refers to apoA-I wherein one or more of the available tyrosine positions thereof is occupied by 3-chlorotyrosine or 3-nitrotyrosine. Antibody with cross reactivity to immobilized oxidized apoA-I can be retained on this column for subsequent removal by a change in elution conditions, whereas eluant which flows through the column comprises antibody which does not react specifically with oxidized apoA-I. By "subsequent removal by a change in elution conditions" is meant any of the conditions known in the art for disruption of antibody-antigen complex including, for example without limitation, change in ionic strength, pH, or concentration of chaotrope. In a subsequent purification step, the eluant from the previous step can be applied to a second column comprising immobilized unoxidized apoA-I. Again, the retained antibody fraction can be removed by subsequent removal by a change in elution conditions.

As understood by those of skill in the art, fragments of oxidized and/or unoxidized apoA-I can serve as immunogen for antibody production. For example, apoA-I nitrated at Tyr$^{192}$ and apoA-I chlorinated at Tyr$^{192}$ (SEQ ID NOs: 78-83) can serve as immunogen for the production of anti-[NO$_2$-Tyr$^{192}$]apoA-I and anti-[Cl-Tyr$^{192}$]apoA-I, respectively.

In an alternative antibody production scheme, a fragment of apoA-I not comprising an oxidizable tyrosine could serve as immunogen for the production of anti-(unoxidized)-apoA-I, and, for example without limitation, target fragment LAEY-HAK (Entry 79, Table 1, Residues 2-8 of SEQ ID NO: 81) nitrated or chlorinated at Tyr$^{192}$ can serve as immunogen for the production of anti-(oxidized)-apoA-I.

Monoclonal antibodies to the target antigen such as apoA-I also may be prepared using methods well known in the art. Commercially available antibodies are commonly available and may be used as well.

A.2. —Antibody Reaction

In a typical experiment, antibody to apoA-I, produced by, for example without limitation, any of the methods described herein, can be bound to protein A and cross-linked with dimethylpimelimidate prior to packing in an antibody column. The biological sample containing target protein apoA-I can be applied to the antibody column in, for example without limitation, 0.15 M NaCl, 0.1 M phosphate, pH 7.2 buffer. apoA-I in both oxidized and unoxidized form can be retained on the column and subsequently removed by a change in elution condition to provide substantially purified target protein apoA-I.

B.1. —Aptamer Production

In a typical experiment, aptamer produced against apoA-I would comprise an initial oligomer pool comprising random sequences of 3 to 40 nucleotides in length and flanking sequences for PCR amplification of from 3 to 10 sequences in length. Three to six rounds of selection/amplification would be conducted, and the resulting aptamers would be cloned and sequenced for determination of consensus sequence. Aptamers contained the consensus sequences would be produced by conventional synthetic or recombinant techniques well known in the art.

B.2. —Aptamer Reaction

Aptamer fractions containing consensus sequences would be covalently attached to a solid support, as for example without limitation a chromatographic column affinity matrix, using conventional methods. ApoA-I sample could be applied directly to the aptamer column so formed resulting in retention of apoA-I which could be subsequently separated by a change in elution conditions as, for example without limitation, a change in pH or ionic strength. In an alternative procedure, derivatized aptamer and apoA-I sample could be mixed in solution with subsequent isolation of aptamer-apoA-I complex by any of the methods known in the art and/or described herein.

Example 3

Fragmentation of apoA-I

The sample of Example 1, optionally enriched in apoA-I as exemplified in Example 2, can be incubated in a reaction mixture with trypsin overnight at 37 degrees Celcius to afford target fragments. After incubation, in an optional step, the reaction mixture can be passed over a C$_{18}$ HPLC column with monitoring of the peptide backbone absorption at, e.g., 208 nm, in order to identify target fragment elution. Fractions rich in target fragments can then be collected for subsequent analyses.

As an alternative method of production of target fragments, sample containing apoA-I can be directly introduced into an MS/MS mass spectrometer. Cleavage of peptide backbone bonds by any of the mechanisms of bond dissociation discussed herein and well known in the art can result in fragments of known mass and known sequence. Selection based on mass and containment of selected fragments within a quadrapole ion trap then can provide target fragments for subsequent analyses. Target fragments would be selected based on the inclusion therein of potentially oxidized amino acid residues.

Example 4

Apolipoprotein A-I Trypsin Cleavage Sites

The sequence of human apolipoprotein A-I (GenPept sequence NP_000030) is a 267-amino acid preprotein:

(SEQ ID NO: 1)
```
  1 MKAAVLTLAV LFLTGSQARH FWQQDEPPQS PWDRVKDLAT VYVDVLKDSG RDYVSQFEGS

61 ALGKQLNLKL LDNWDSVTST FSKLREQLGP VTQEFWDNLE KETEGLRQEM SKDLEEVKAK

121 VQPYLDDFQK KWQEEMELYR QKVEPLRAEL QEGARQKLHE LQEKLSPLGE EMRDRARAHV
```

-continued

```
181 DALRTHLAPY SDELRQRLAA RLEALKENGG ARLAEYHAKA TEHLSTLSEK AKPALEDLRQ

241 GLLPVLESFK VSFLSALEEY TKKLNTQ
```

Post-translation removal of the signal sequence (residues 1-18) and the prosegment (residues 19-24) provides mature apoA-I protein, within which there are 21 naturally occurring lysine and 16 arginine residues indicated by underlining in the sequence following (SEQ ID NO: 2):

```
1          11         21         31         41         51         61
DEPPQSPWDR VKDLATVYVD VLKDSGRDYV SQFEGSALGK QLNLKLLDNW DSVTSTFSKL REQLGPVTQE 71         81         91         101        111        121        131
FWDNLEKETE GLRQEMSKDL EEVKAKVQPY LDDFQKKWQE EMELYRQKVE PLRAELQEGA RQKLHELQEK 141        151        161        171        181        191        201
LSPLGEEMRD RARAHVDALR THLAPYSDEL RQRLAARLEA LKENGGARLA EYHAKATEHL STLSEKAKPA 211        221        231        241
LEDLRQGLLP VLESFKVSFL SALEEYTKKL NTQ
```

Assuming digestion with trypsin by methods well known in the art of protein chemistry, a maximum of two missed cleavages, a minimum digest fragment length of 5 residues, and fragment mass in the range 800-4000 Dalton, 96 fragments from the digestion, shown in Table 1, would result. The results shown in Table 1 are merely exemplary of the peptide fragments which could be obtained by proteolytic digestion and are not limiting to the scope of the claimed invention. The skilled artisan could easily manipulate the conditions, for example time of incubation, protease and protein concentration, temperature, ionic strength and the like, to obtain different sized fragments using trypsin or another protease well known in the art to obtain fragments different from those of Table 1.

TABLE 1

Theoretical fragmentation resulting from trypsin digestion of apoA-I.

| # | Mass1 | Mass2 | Start | End | MC | Sequence | SEQ ID |
|---|---|---|---|---|---|---|---|
| 1 | 1226.54 | 1227.28 | 1 | 10 | 0 | (-)DEPPQSPWDR(V) | SEQ ID NO: 3 |
| 2 | 1453.71 | 1454.59 | 1 | 12 | 1 | (-)DEPPQSPWDRVK(D) | SEQ ID NO: 4 |
| 3 | 2670.38 | 2672.03 | 1 | 23 | 2 | (-)DEPPQSPWDRVKDLATVYVDVLK(D) | SEQ ID NO: 5 |
| 4 | 1462.85 | 1463.77 | 11 | 23 | 1 | (R)VKDLATVYVDVLK(D) | SEQ ID NO: 6 |
| 5 | 1878.03 | 1879.18 | 11 | 27 | 2 | (R)VKDLATVYVDVLKDSGR(D) | SEQ ID NO: 7 |
| 6 | 1235.69 | 1236.46 | 13 | 23 | 0 | (K)DLATVYVDVLK(D) | SEQ ID NO: 8 |
| 7 | 1650.87 | 1651.87 | 13 | 27 | 1 | (D)DLATVYVDVLKDSGR(D) | SEQ ID NO: 9 |
| 8 | 3032.52 | 3034.37 | 13 | 40 | 2 | (K)DLATVYVDVLKDSGRDYVSQFEGSALGK(Q) | SEQ ID NO: 10 |
| 9 | 1815.85 | 1816.93 | 24 | 40 | 1 | (K)DSGRDYVSQFEGSALGK(Q) | SEQ ID NO: 11 |
| 10 | 2412.22 | 2413.67 | 24 | 45 | 2 | (K)DSGRDYVSQFEGSALGKQLNLK(L) | SEQ ID NO: 12 |
| 11 | 1400.67 | 1401.53 | 28 | 40 | 0 | (R)DYVSQFEGSALGK(Q) | SEQ ID NO: 13 |
| 12 | 1997.03 | 1998.26 | 28 | 45 | 1 | (R)DYVSQFEGSALGKQLNLK(L) | SEQ ID NO: 14 |
| 13 | 3590.80 | 3593.01 | 28 | 59 | 2 | (R)DYVSQFEGSALGKQLNLKLLDNWDSVTSTFSK(L) | SEQ ID NO: 15 |
| 14 | 2192.12 | 2193.48 pE | 41 | 59 | 1 | (K)QLNLKLLDNWDSVTSTFSK(L) | SEQ ID NO: 16 |
| 15 | 2209.15 | 2210.51 | 41 | 59 | 1 | (K)QLNLKLLDNWDSVTSTFSK(L) | SEQ ID NO: 17 |
| 16 | 2461.31 | 2462.83 pE | 41 | 61 | 2 | (K)QLNLKLLDNWDSVTSTFSKLR(E) | SEQ ID NO: 18 |
| 17 | 2478.35 | 2479.86 | 41 | 61 | 2 | (K)QLNLKLLDNWDSVTSTFSKLR(E) | SEQ ID NO: 19 |
| 18 | 1612.79 | 1613.78 | 46 | 59 | 0 | (K)LLDNWDSVTSTFSK(L) | SEQ ID NO: 20 |
| 19 | 1881.97 | 1883.12 | 46 | 61 | 1 | (K)LLDNWDSVTSTFSKLR(E) | SEQ ID NO: 21 |
| 20 | 3795.89 | 3798.23 | 46 | 77 | 2 | (K)LLDNWDSVTSTFSKLREQLGPVTQEFWDNLEK(E) | SEQ ID NO: 22 |

TABLE 1-continued

Theoretical fragmentation resulting from trypsin digestion of apoA-I.

| | | | | | | |
|---|---|---|---|---|---|---|
| 21 | 2202.12 | 2203.48 | | 60 77 1 | (K)LREQLGPVTQEFWDNLEK(E) | SEQ ID NO: 23 |
| 22 | 2887.46 | 2889.21 | | 60 83 2 | (K)LREQLGPVTQEFWDNLEKETEGLR(Q) | SEQ ID NO: 24 |
| 23 | 1932.93 | 1934.13 | | 62 77 0 | (R)EQLGPVTQEFWDNLEK(E) | SEQ ID NO: 25 |
| 24 | 2618.27 | 2619.87 | | 62 83 1 | (R)EQLGPVTQEFWDNLEKETEGLR(Q) | SEQ ID NO: 26 |
| 25 | 3221.54 | 3223.57 | | 62 88 2 | (R)EQLGPVTQEFWDNLEKETEGLRQEMSK(D) | SEQ ID NO: 27 |
| 26 | 1307.63 | 1308.46 | | 78 88 1 | (K)ETEGLRQEMSK(D) | SEQ ID NO: 28 |
| 27 | 2020.99 | 2022.25 | | 78 94 2 | (K)ETEGLRQEMSKDLEEVK(A) | SEQ ID NO: 29 |
| 28 | 1318.62 | 1319.48 | pE | 84 94 1 | (R)QEMSKDLEEVK(A) | SEQ ID NO: 30 |
| 29 | 1335.65 | 1336.51 | | 84 94 1 | (R)QEMSKDLEEVK(A) | SEQ ID NO: 31 |
| 30 | 1517.75 | 1518.74 | pE | 84 96 2 | (R)QEMSKDLEEVKAK(V) | SEQ ID NO: 32 |
| 31 | 1534.78 | 1535.77 | | 84 96 2 | (R)QEMSKDLEEVKAK(V) | SEQ ID NO: 33 |
| 32 | 931.51 | 932.07 | | 89 96 1 | (K)DLEEVKAK(V) | SEQ ID NO: 34 |
| 33 | 2165.11 | 2166.45 | | 89 106 2 | (K)DLEEVKAKVQPYLDDFQK(K) | SEQ ID NO: 35 |
| 34 | 1451.75 | 1452.66 | | 95 106 1 | (K)AKVQPYLDDFQK(K) | SEQ ID NO: 36 |
| 35 | 1579.85 | 1580.84 | | 95 107 2 | (K)AKVQPYLDDFQKK(W) | SEQ ID NO: 37 |
| 36 | 1252.62 | 1253.41 | | 97 106 0 | (K)QVPYLDDFQK(K) | SEQ ID NO: 38 |
| 37 | 1380.72 | 1381.58 | | 97 107 1 | (K)QVPYLDDFQKK(W) | SEQ ID NO: 39 |
| 38 | 2645.27 | 2647.00 | | 97 116 2 | (K)VQPYLDDFQKKWQEEMELYR(Q) | SEQ ID NO: 40 |
| 39 | 1411.67 | 1412.62 | | 107 116 1 | (K)KWQEEMELYR(Q) | SEQ ID NO: 41 |
| 40 | 1667.82 | 1668.92 | | 107 118 2 | (K)KWQEEMELYRQK(V) | SEQ ID NO: 42 |
| 41 | 1283.57 | 1284.44 | | 108 116 0 | (K)WQEEMELYR(Q) | SEQ ID NO: 43 |
| 42 | 1539.73 | 1540.75 | | 108 118 1 | (K)WQEEMELYRQK(V) | SEQ ID NO: 44 |
| 43 | 2134.08 | 2135.47 | | 108 123 2 | (K)WQEEMELYRQKVEPLR(A) | SEQ ID NO: 45 |
| 44 | 852.49 | 853.02 | pE | 117 123 1 | (R)QKVEPLR(A) | SEQ ID NO: 46 |
| 45 | 869.52 | 870.05 | | 117 123 1 | (R)QKVEPLR(A) | SEQ ID NO: 47 |
| 46 | 1706.92 | 1707.94 | pE | 117 131 2 | (R)QKVEPLRAELQEGAR(Q) | SEQ ID NO: 48 |
| 47 | 1723.95 | 1724.97 | | 117 131 2 | (R)QKVEPLRAELQEGAR(Q) | SEQ ID NO: 49 |
| 48 | 1467.79 | 1468.66 | | 119 131 1 | (K)VEPLRAELQEGAR(Q) | SEQ ID NO: 50 |
| 49 | 1723.95 | 1724.97 | | 119 133 2 | (K)VEPLRAELQEGARQK(L) | SEQ ID NO: 51 |
| 50 | 873.44 | 873.95 | | 124 131 0 | (R)AELQEGAR(Q) | SEQ ID NO: 52 |
| 51 | 1129.60 | 1130.25 | | 124 133 1 | (R)AELQEGARQK(L) | SEQ ID NO: 53 |
| 52 | 2007.06 | 2008.26 | | 124 140 2 | (R)AELQEGARQKLHELQEK(L) | SEQ ID NO: 54 |
| 53 | 1135.61 | 1136.30 | pE | 132 140 1 | (R)QKLHELQEK(L) | SEQ ID NO: 55 |
| 54 | 1152.64 | 1153.33 | | 132 140 1 | (R)QKLHELQEK(L) | SEQ ID NO: 56 |
| 55 | 2148.11 | 2149.49 | pE | 132 149 2 | (R)QKLHELQEKLSPLGEEMR(D) | SEQ ID NO: 57 |
| 56 | 2165.14 | 2166.52 | | 132 149 2 | (R)QKLHELQEKLSPLGEEMR(D) | SEQ ID NO: 58 |
| 57 | 896.48 | 897.03 | | 134 140 0 | (K)LHELQEK(L) | SEQ ID NO: 59 |
| 58 | 1908.99 | 1910.21 | | 134 149 1 | (K)LHELQEKLSPLGEEMR(D) | SEQ ID NO: 60 |
| 59 | 2180.11 | 2181.49 | | 134 151 2 | (K)LHELQEKLSPLGEEMRDR(A) | SEQ ID NO: 61 |

TABLE 1-continued

Theoretical fragmentation resulting from trypsin digestion of apoA-I.

| | | | | | | | | |
|---|---|---|---|---|---|---|---|---|
| 60 | 1031.52 | 1032.21 | | 141 | 149 | 0 | (K)LSPLGEEMR(D) | SEQ ID NO: 62 |
| 61 | 1302.65 | 1303.49 | | 141 | 151 | 1 | (K)LSPLGEEMRDR(A) | SEQ ID NO: 63 |
| 62 | 1529.79 | 1530.76 | | 141 | 153 | 2 | (K)LSPLGEEMRDRAR(A) | SEQ ID NO: 64 |
| 63 | 1279.70 | 1280.44 | | 150 | 160 | 2 | (R)DRARAHVDALR(T) | SEQ ID NO: 65 |
| 64 | 1008.57 | 1009.16 | | 152 | 160 | 1 | (R)ARAHVDALR(T) | SEQ ID NO: 66 |
| 65 | 2291.20 | 2292.58 | | 152 | 171 | 2 | (R)ARAHVDALRTHLAPYSDELR(Q) | SEQ ID NO: 67 |
| 66 | 2064.06 | 2065.31 | | 154 | 171 | 1 | (R)AHVDALRTHLAPYSDELR(Q) | SEQ ID NO: 68 |
| 67 | 2348.22 | 2349.63 | | 154 | 173 | 2 | (R)AHVDALRTHLAPYSDELRQR(L) | SEQ ID NO: 69 |
| 68 | 1301.65 | 1302.44 | | 161 | 171 | 0 | (R)THLAPYSDELR(Q) | SEQ ID NO: 70 |
| 69 | 1585.81 | 1586.76 | | 161 | 173 | 1 | (R)THLAPYSDELRQR(L) | SEQ ID NO: 71 |
| 70 | 1997.07 | 1998.27 | | 161 | 177 | 2 | (R)THLAPYSDELRQRLAAR(L) | SEQ ID NO: 72 |
| 71 | 1251.75 | 1252.51 | pE | 172 | 182 | 2 | (R)QRLAARLEALK(E) | SEQ ID NO: 73 |
| 72 | 1268.78 | 1269.54 | | 172 | 182 | 2 | (R)QRLAARLEALK(E) | SEQ ID NO: 74 |
| 73 | 984.62 | 985.22 | | 174 | 182 | 1 | (R)LAARLEALK(E) | SEQ ID NO: 75 |
| 74 | 1568.89 | 1569.82 | | 174 | 188 | 2 | (R)LAARLEALKENGGAR(L) | SEQ ID NO: 76 |
| 75 | 1157.63 | 1158.31 | | 178 | 188 | 1 | (K)LEALKENGGAR(L) | SEQ ID NO: 77 |
| 76 | 1970.05 | 1971.24 | | 178 | 195 | 2 | (K)LEALKENGGARLAEYHAK(A) | SEQ ID NO: 78 |
| 77 | 1415.70 | 1416.55 | | 183 | 195 | 1 | (K)ENGGARLAEYHAK(A) | SEQ ID NO: 79 |
| 78 | 2612.31 | 2613.86 | | 183 | 206 | 2 | (K)ENGGARLAEYHAKATEHLSTLSEK(A) | SEQ ID NO: 80 |
| 79 | 831.44 | 831.95 | | 189 | 195 | 0 | (R)LAEYHAK(A) | SEQ ID NO: 81 |
| 80 | 2028.04 | 2029.27 | | 189 | 206 | 1 | (R)LAEYHAKATEHLSTLSEK(A) | SEQ ID NO: 82 |
| 81 | 3021.60 | 3023.44 | | 189 | 215 | 2 | (R)LAEYHAKATEHLSTLSEKAKPALEDLR(Q) | SEQ ID NO: 83 |
| 82 | 1215.62 | 1216.34 | | 196 | 206 | 0 | (K)ATEHLSTLSEK(A) | SEQ ID NO: 84 |
| 83 | 2209.18 | 2210.51 | | 196 | 215 | 1 | (K)ATEHLSTLSEKAKPALEDLR(Q) | SEQ ID NO: 85 |
| 84 | 3420.87 | 3422.97 | | 196 | 226 | 2 | (K)ATEHLSTLSEKAKPALEDLRQGLLPVLESFK(V) | SEQ ID NO: 86 |
| 85 | 1012.58 | 1013.19 | | 207 | 215 | 0 | (K)AKPALEDLR(Q) | SEQ ID NO: 87 |
| 86 | 2224.27 | 2225.65 | | 207 | 226 | 1 | (K)AKPALEDLRQGLLPVLESFK(V) | SEQ ID NO: 88 |
| 87 | 2591.97 | 3594.21 | | 207 | 238 | 2 | (K)AKPALEDLRQGLLPVLESFKVSFLSALEEYTK(K) | SEQ ID NO: 89 |
| 88 | 1213.68 | 1214.46 | pE | 216 | 226 | 0 | (R)QGLLPVLESFK(V) | SEQ ID NO: 90 |
| 89 | 1230.71 | 1231.49 | | 216 | 226 | 0 | (R)QGLLPVLESFK(V) | SEQ ID NO: 91 |
| 90 | 2581.38 | 2583.02 | pE | 216 | 238 | 1 | (R)QGLLPVLESFKVSFLSALEEYTK(K) | SEQ ID NO: 92 |
| 91 | 2598.41 | 2600.05 | | 216 | 238 | 1 | (R)QGLLPVLESFKVSFLSALEEYTK(K) | SEQ ID NO: 93 |
| 92 | 2709.48 | 2711.19 | pE | 216 | 239 | 2 | (R)QGLLPVLESFKVSFLSALEEYTKK(L) | SEQ ID NO: 94 |
| 93 | 2726.50 | 2728.22 | | 216 | 239 | 2 | (R)QGLLPVLESFKVSFLSALEEYTKK(L) | SEQ ID NO: 95 |
| 94 | 1368.72 | 1387.58 | | 227 | 238 | 0 | (K)VSFLSALEEYTK(K) | SEQ ID NO: 96 |

TABLE 1-continued

Theoretical fragmentation resulting from trypsin digestion of apoA-I.

| 95 | 1514.81 | 1515.76 | 227 239 1 | (K)VSFLSALEEYTKK(L) | SEQ ID NO: 97 |
| 96 | 1971.04 | 1972.26 | 227 243 2 | (K)VSFLSALEEYTKKLNTQ(-) | SEQ ID NO: 98 |

Column 1: Index number.
Column 2: m/z (main isotope).
Column 3: m/z (average).
Column 4: pE: N-terminal glutamine reported as pyroglutamic acid.
Column 5: Starting residue number in apoA-I sequence (SEQ ID NO: 2)
Column 6: Ending residue number in apoA-I sequence. (SEQ ID NO: 2)
Column 7: Number of missed potential trypsin cleavage sites.
Column 8: Target fragment sequence; residues in parentheses indicate adjacent residues not in target fragment sequence; (-) indicates N- or C-terminal.
Column 9: Sequence identification numbers of target fragments.

As provided in Table 1, digestion with trypsin under the conditions indicated for Table 1 provides 96 target fragments of predicted amino acid sequence. Of these 96 target fragments, 42 (i.e., fragments 3-13, 33-43, 65-70, 76-81, 87, and 90-96 of Table 1) comprise at least one tyrosine. Of these 42 fragments, six (i.e., fragments 76-81 of Table 1) comprise $Tyr^{192}$ of apoA-I (SEQ ID NOs: 78-83).

Accordingly, Table 2 (target fragments 76-81 of Table 1) provides the main isotope m/z for each target fragment comprising $Tyr^{192}$ for unoxidized (Col. 2), chlorinated (Col. 3) and nitrated (Col. 4) forms of $Tyr^{192}$ of apoA-I (SEQ ID NOs: 78-83).

TABLE 2

Theoretical observable masses for fragments 76-81 of Table L

| 76 | 1970.1 | 2004.0 | 2015.0 | 178 198 | (R)LEALKENGGARLAEYHAK(A) | SEQ ID NO: 78 |
| 77 | 1415.7 | 1449.7 | 1460.7 | 183 195 | (K)ENGGARLAEYHAK(A) | SEQ ID NO: 79 |
| 78 | 2612.3 | 2646.3 | 2657.3 | 183 206 | (K)ENGGARLAEYHAKATEHLSTLSEK(A) | SEQ ID NO: 80 |
| 79 | 831.4 | 865.4 | 876.4 | 189 195 | (R)LAEYHAK(A) | SEQ ID NO: 81 |
| 80 | 2028.0 | 2062.0 | 2073.0 | 189 206 | (R)LAEYHAKATEHLSTLSEK(A) | SEQ ID NO: 82 |
| 81 | 3021.6 | 3055.6 | 3066.6 | 189 215 | (R)LAEYHAKATEHLSTLSEKAKPALEDLR(Q) | SEQ ID NO: 83 |

Column 1: Index number.
Column 2: m/z (unoxidized) $[M + H]^+$.
Column 3: m/z (chlorinated $Tyr^{192}$ SEQ ID NO: 2)$[M + Cl]^+$
Column 4: m/z (nitrated $Tyr^{192}$ SEQ ID NO: 2) $[M + NO_2]^+$
Column 5: Starting residue number in apoA-I sequence.
Column 6: Ending residue number in apoA-I sequence.
Column 7: Target fragment sequence; residues in parentheses indicate adjacent residues not in target fragment sequence; (-) indicates N- or C-terminal.
Column 8: Sequence identification numbers of target fragments.

The extent of oxidation of $Tyr^{192}$ (SEQ ID NO: 2) can be calculated from the amount of 3-chlorotyrosine and 3-nitrotyrosine relative to the total amount of naturally occurring Tyr any of target fragments 76-81 (Table 2).

Example 5

Sample Preparation for Mass Spectrometry

In a typical experiment, reaction mixture containing target fragments could be separated by a reverse-phase capillary HPLC (50-μm-i.d., 10-μm-tip, 6 cm length) packed with $C_{18}$ packing material as routinely employed in the art. Elution could employ a gradient protocol, for example without limitation, 2-70% acetonitrile in 50 mM acetic acid over 45-min.

Example 6

Mass Spectrometry of Target Fragments

In a typical experiment, the reaction mixture containing potentially oxidized target fragments can be analyzed by employing the capillary column HPLC protocol of Example 5 in combination with a tandem mass spectrometer. The mass spectrometer could be operated in MS/MS mode. Sample introduction can employ nanospray electrostatic ionization with a flow rate of, for example without limitation, 200 mL/min. Fragments with excess mass corresponding to chlorination or nitration at position 3 of the aromatic ring of tyrosine can be identified by computer based analysis programs long known in the art of mass spectrometry. In some cases, all tyrosines of apoA-I are analyzed for oxidation. In other cases, representative tyrosines are analyzed. In some embodiments, the masses of fragments of apoA-I comprising $Tyr^{192}$ (SEQ ID NO: 78-83) are analyzed.

Example 7

Calculation of Oxidation Status

In a typical experiment, the relative abundance of unoxidized, chlorinated, and nitrated tyrosine is calculated from the observed MS/MS fragmentation pattern. These calculations can rely on the observation of a single target fragment comprising a specific tyrosine residue, or multiple target fragments each comprising a specific tyrosine residue. Additionally, these calculations can rely on the observation of a single target fragment comprising a plurality of specific tyrosine residues, or multiple target fragments each comprising a plurality of specific tyrosine residues.

As an example, if the results of MS/MS analysis showed that the integrated intensities for a target fragment having only a single tyrosine present in the form of tyrosine, 3-chlorotyrosine, and 3-nitrotyrosine, are 1000, 350 and 650, respectively, the total amount is (1000+350+650)=2000, the extent of oxidation is (350+650)=1000, and the oxidation status is (extent of oxidation)/(total amount)=1000/2000=50%.

In another example, if a target fragment contains two tyrosines which are the only tyrosines within the fragment, and mass spectrometric analysis reveals the following target fragment integrated intensities

| Oxidation state | integrated intensity |
|---|---|
| no oxidation | 500 |
| 1 [3-chloro]-Tyr | 1000 |
| 2 [3-chloro]-Tyr | 400 |
| 1 [3-chloro]-Tyr & 1 [3-nitro]-Tyr | 300 |
| 1 [3-nitro]-Tyr | 200 |
| 2 [3-nitro]-Tyr | 100 | then the total amount is (500+1000+400+300+200+100)= 2500, the extent of oxidation is (1000+400+300+200+100)= 2000, and the oxidation status is (extent of oxidation)/(total amount)=2000/2500=80%.

Example 8

Quantitation of Total Oxidized apoA-I

The oxidation status of apoA-I in a biological sample can be determined by methods described herein and expressed as an oxidation fraction. The amount, or alternatively concentration, of apoA-I in the biological sample can be determined by standard immunoassay methods known in the art. Reagents for immunoassay of apoA-I are readily available, e.g., in vitro diagnostic reagent (catalog OEUD15) for the quantitative determination of apoA-I in human serum with nephelometer systems from Dade Behring. Total oxidized apoA-I can be reported as the multiplicative product of oxidation fraction and total amount of apoA-I in the biological sample.

Example 9

Calculation of Risk Potential for CVD

In the first case of Example 7, the risk potential would be reported as 50%, wherein 0% corresponds to no excess risk potential due to oxidized apoA-I, and 100% corresponds to the greatest excess risk potential due to oxidized apoA-I. In the second case of Example 7, the risk potential would be reported as 80%.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention. Other embodiments are set forth within the following claims.

What is claimed is:

1. A method for quantitating the amount of oxidized apolipoprotein A-I in a biological sample obtained from a human, comprising:
   determining the amount in the biological sample of an oxidized apolipoprotein A-I target fragment wherein said target fragment consists fragment selected from the group consisting of SEQ ID NOs: 78-80, 82, and 83, wherein said target fragment comprises at least one oxidized amino acid residue.

2. The method of claim 1, wherein determining the amount of the target fragment comprises quantitation of the target fragment using mass spectrometry.

3. The method of claim 2, wherein the mass spectrometry comprises generating an ion of the apolipoprotein A-I target fragment selected from the group consisting of ions with mass-to-charge ratio (m/z) of 2004.0±0.5, 1449.7±0.5, 2646.3±0.5, 2062.0±0.5, and 3055.6±0.5.

4. The method of claim 2, wherein the mass spectrometry comprises generating an ion of the apolipoprotein A-I target fragment selected from the group consisting of ions with m/z of 2015.0±0.5, 1460.7±0.5, 2657.3±0.5, 2073.0±0.5, and 3066.6±0.5.

5. The method of claim 2, wherein the mass spectrometry is tandem mass spectrometry.

6. The method of claim 1, wherein the biological sample is plasma or serum.

7. The method of claim 1, wherein the apolipoprotein A-I is digested with a protease to form the apolipoprotein A-I fragment.

8. The method of claim 7, wherein the protease is selected from the group consisting of trypsin, chymotrypsin, papain, pepsin, and thermolysin.

9. The method of claim 8, wherein the protease is trypsin.

10. The method of claim 1, wherein the oxidized amino acid residue is selected from the group consisting of chlorinated tyrosine and nitrated tyrosine.

11. The method of claim 1, further comprising enriching the apolipoprotein A-I in the biological sample.

12. The method of claim 11, wherein enriching comprises affinity purification.

13. The method of claim 12, wherein the affinity purification comprises the use of an affinity agent selected from the group consisting of aptamer and antibody.

14. A method for assessing risk of cardiovascular disease for a human subject comprising:
   (a) determining a total amount of apolipoprotein A-I in a biological sample from the subject by quantifying the amount of an apolipoprotein A-I target fragment wherein said target fragment consists fragment selected from the group consisting of SEQ ID NOs: 78-80, 82, and 83;
   (b) determining the oxidized proportion of the amount of apolipoprotein A-I in the biological sample by quantifying the amount of the apolipoprotein A-I target fragment that comprises at least one oxidized amino acid residue and relating the amount of the apolipoprotein A-I target fragment that comprises at least one oxidized amino acid residue to the total amount of apolipoprotein A-I; and
   (c) assessing risk of cardiovascular disease in the subject based on the oxidized proportion, wherein a larger oxidized proportion of apoA-I indicates a higher risk of cardiovascular disease.

15. The method of claim 14, wherein the amount of the apolipoprotein A-1 fragment is quantified using mass spectrometry.

16. The method of claim 15, wherein the mass spectrometry comprises generating an ion of the apolipoprotein A-I target fragment selected from the group consisting of ions with mass-to-charge ratios (m/z) of 2004.0±0.5, 1449.7±0.5, 2646.3±0.5, 2062.0±0.5, and 3055.6±0.5.

17. The method of claim 15, wherein the mass spectrometry comprises generating an ion of the apolipoprotein target fragment ion selected from the group consisting of ions with m/z of 2015.0±0.5, 1460.7±0.5, 2657.3±0.5, 2073.0±0.5, and 3066.6±0.5.

18. The method of claim 15, wherein the mass spectrometry is tandem mass spectrometry.

19. The method of claim 14, wherein the biological sample is plasma or serum.

20. The method of claim 14, wherein the apolipoprotein A-I is digested with a protease to form the apolipoprotein A-I fragment.

21. The method of claim 20, wherein the protease is selected from the group consisting of trypsin, chymotrypsin, papain, pepsin, and thermolysin.

22. The method of claim 21, wherein the protease is trypsin.

23. The method of claim 14, wherein the oxidized amino acid residue is selected from the group consisting of chlorinated tyrosine and nitrated tyrosine.

24. The method of claim 14, further comprising enriching the apolipoprotein A-I in the biological sample.

25. The method of claim 24, wherein enriching comprises affinity purification.

26. The method of claim 25, wherein the affinity purification comprises the use of an affinity agent selected from the group consisting of aptamer and antibody.

* * * * *